(12) United States Patent
Dubin et al.

(10) Patent No.: US 6,455,278 B1
(45) Date of Patent: Sep. 24, 2002

(54) DNA ENCODING HUMAN VANILLOID RECEPTOR VR3

(75) Inventors: Adrienne Elizabeth Dubin, San Diego; Arne Huvar, La Mesa; Charles A. Glass, San Diego; Mark G. Erlander, Encinitas, all of CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/500,123

(22) Filed: Feb. 8, 2000

(51) Int. Cl.$^7$ .......................... C12N 15/12; C12N 5/10; C12N 15/63; C07K 14/705
(52) U.S. Cl. .................... 435/69.1; 536/23.1; 435/71.2; 435/325; 435/252.3; 435/254.11; 435/471; 435/320.1
(58) Field of Search ............................... 536/23.1, 23.5; 530/356; 435/69.1, 71.1, 71.2, 471, 325, 252.3, 254.11, 320.1

(56) References Cited

FOREIGN PATENT DOCUMENTS

| WO | WO 99/37765 | 7/1999 |
|---|---|---|

OTHER PUBLICATIONS

Mikayama et al. Proc. Natl Acad. Sci. USA vol. 90, pp. 10056–10060, 1993.*

Voet et al. Biochemistry. John Wiley & Sons Inc. pp. 126–128 and 228–234, 1990.*

Bevan, S.; Hothi, S; Hughes, I.F.; James, H.P.; Rang, Shah K.; Walpole, C.S.J.; Yeats, J.C. Capsazepine: a competitive antagonist of the sensory neurone excitant capsaicin. Br. J. Pharmacol, 107, 544–522, 1992.

Bevan, Stuart; Szolcsanyi, Janos. Sensory neuron–specific actions of cpsaicin: mechanisms and applications. TiPS—vol. 11, Aug. 1990.

Caterina, Michael J.; Rosen, Tobias A.; Tominaga, Makoto; Brake, Anthony J.; Julius, David. A capsaicin–receptor homologue with a high threhold for noxious heat. Letters to Nature, vol. 398, Apr. 1, 1999.

Gupta, P.D.; Pushkala, K. Importance of the role of calcium in programmed cell death: a review. Cytobios 99, 83–95, 1999.

Leeman, Susan E,; Krause, James E.; Lembeck, Fred. Substance P and Related Peptides: Cellular and Molecular Physiology. Annals of the New York Academy of Sciences, vol. 632, 1991.

Minke, Baruch; Selinger; Zvi. The roles of trp and calcium in regulating photoreceptor function in Drosphila. Neurobiology, 6:459–466, 1996.

Oh, Uhtaek; Hwang, Sun Wook; Kim, Donghee. Capsaicin Activates a Nonselective Cation Channel in Cultured Neonatal Rat Dorsal Ganglion Neurons. The Journal of Neurosciences, 16 (5): 1659–1667, Mar. 1, 1996.

Szallasi M.D., Arpad. Autoradiographic visualization and pharmacological characterization of vannilloid (capsaicin)n receptors in several species, including man. ACTA Physiologica Scandinavica, Supplementum 629, Stockholm, 1995.

Szolcsanyi, Janos. Capsaicin–sensitive sensory nerve terminals with local and systemic efferent functions: facts and scopes of an unorthodox neuroregulatory mechanism. Progress in Brain Research, vol. 113, Elsevier Science BV. 1996.

Tominaga, Makoto; Caterina, Michael J.; Malmberg, Annika B.; Rosen, Tobias A.; Gilbert, Heather; Skinner, Kate; Raumann, Brigitte E.; Basbaum, Allan I.; Julius, David. The Cloned Capsaicin Receptor Integrates Multiple Pain–Producing Stimuli. Neuron, vol. 21, 531–543, Sep., 1998.

Wood, John N.; Winter, Janet; James, Lain F.; Rang, Humphrey P.; Yates, Jane; Bevan, Stuart. Capsaicin–Induced Ion Fluxes in Dorsal Root Ganglion Cells in Culture. The Journal of Neoroscience, 8(9): 3206–3220, Sep., 1988.

* cited by examiner

*Primary Examiner*—Prema Mertz
(74) *Attorney, Agent, or Firm*—John W. Wallen, III

(57) ABSTRACT

DNA encoding human VR1 receptor has been cloned and characterized. The recombinant protein is capable of forming biologically active protein. The cDNA's have been expressed in recombinant host cells that produce active recombinant protein. The recombinant protein is also purified from the recombinant host cells. In addition, the recombinant host cells are utilized to establish a method for identifying modulators of the receptor activity, and receptor modulators are identified.

9 Claims, 18 Drawing Sheets

FIG. 1A

SEQ.ID.NO.5.
Human VR3A+B- nucleotide sequence of the coding sequence
(2616 bp).

ATGGCGGATTCCAGCGAAGGCCCCCGCGCGGGGCCCGGGGAGGTGGCTGAG
CTCCCCGGGGATGAGAGTGGCACCCCAGGTGGGGAGGCTTTTCCTCTCTCC
TCCCTGGCCAATCTGTTTGAGGGGGAGGATGGCTCCCTTTCGCCCTCACCG
GCTGATGCCAGTCGCCCTGCTGGCCCAGGCGATGGCGACCAAATCTGCGC
ATGAAGTTCCAGGGCGCCTTCCGCAAGGGGGTGCCCAACCCCATCGATCTG
CTGGAGTCCACCCTATATGAGTCCTCGGTGGTGCCTGGGCCCAAGAAAGCA
CCCATGGACTCACTGTTTGACTACGGCACCTATCGTCACCACTCCAGTGAC
AACAAGAGGTGGAGGAAGAAGATCATAGAGAAGCAGCCGCAGAGCCCCAAA
GCCCCTGCCCCTCAGCCGCCCCCATCCTCAAAGTCTTCAACCGGCCTATC
CTCTTTGACATCGTGTCCCGGGGCTCCACTGCTGACCTGGACGGGCTGCTC
CCATTCTTGCTGACCCACAAGAAACGCCTAACTGATGAGGAGTTTCGAGAG
CCATCTACGGGGAAGACCTGCCTGCCCAAGGCCTTGCTGAACCTGAGCAAT
GGCCGCAACGACACCATCCCTGTGCTGCTGGACATCGCGGAGCGCACCGGC
AACATGCGGGAGTTCATTAACTCGCCCTTCCGTGACATCTACTATCGAGGT
CAGACAGCCCTGCACATCGCCATTGAGCGTCGCTGCAAACACTACGTGGAA
CTTCTCGTGGCCCAGGGAGCTGATGTCCACGCCCAGGCCCGTGGGCGCTTC
TTCCAGCCCAAGGATGAGGGGGGCTACTTCTACTTTGGGGAGCTGCCCCTG
TCGCTGGCTGCCTGCACCAACCAGCCCCACATTGTCAACTACCTGACGGAG
AACCCCCACAAGAAGGCGGACATGCGGCGCCAGGACTCGCGAGGCAACACA
GTGCTGCATGCGCTGGTGGCCATTGCTGACAACACCCGTGAGAACACCAAG
TTTGTTACCAAGATGTACGACCTGCTGCTGCTCAAGTGTGCCCGCCTCTTC
CCCGACAGCAACCTGGAGGCCGTGCTCAACAACGACGGCCTCTCGCCCCTC
ATGATGGCTGCCAAGACGGGCAAGATTGGGATCTTTCAGCACATCATCCGG
CGGGAGGTGACGGATGAGGACACACGGCACCTGTCCCGCAAGTTCAAGGAC
TGGGCCTATGGGCCAGTGTATTCCTCGCTTTATGACCTCTCCTCCCTGGAC
ACGTGTGGGGAAGAGGCCTCCGTGCTGGAGATCCTGGTGTACAACAGCAAG
ATTGAGAACCGCCACGAGATGCTGGCTGTGGAGCCCATCAATGAACTGCTG
CGGGACAAGTGGCGCAAGTTCGGGGCCGTCTCCTTCTACATCAACGTGGTC
TCCTACCTGTGTGCCATGGTCATCTTCACTCTCACCGCCTACTACCAGCCG
CTGGAGGGCACACCGCCGTACCCTTACCGCACCACGGTGGACTACCTGCGG
CTGGCTGGCGAGGTCATTACGCTCTTCACTGGGGTCCTGTTCTTCATCACC
AACATCAAAGACTTGTTCATGAAGAAATGCCCTGGAGTGAATTCTCTCTTC
ATTGATGGCTCCTTCCAGCTGCTCTACTTCATCTACTCTGTCCTGGTGATC
GTCTCAGCAGCCCTCTACCTGGCAGGGATCGAGGCCTACCTGGCCGTGATG

FIG. 1B

```
GTCTTTGCCCTGGTCCTGGGCTGGATGAATGCCCTTTACTTCACCCGTGGG
CTGAAGCTGACGGGGACCTATAGCATCATGATCCAGAAGATTCTCTTCAAG
GACCTTTTCCGATTCCTGCTCGTCTACTTGCTCTTCATGATCGGCTACGCT
TCAGCCCTGGTCTCCCTCCTGAACCCGTGTGCCAACATGAAGGTGTGCAAT
GAGGACCAGACCAACTGCACAGTGCCCACTTACCCCTCGTGCCGTGACAGC
GAGACCTTCAGCACCTTCCTCCTGGACCTGTTTAAGCTGACCATCGGCATG
GGCGACCTGGAGATGCTGAGCAGCACCAAGTACCCCGTGGTCTTCATCATC
CTGCTGGTGACCTACATCATCCTCACCTTTGTGCTGCTCCTCAACATGCTC
ATTGCCCTCATGGGCGAGACAGTGGGCCAGGTCTCCAAGGAGAGCAAGCAC
ATCTGGAAGCTGCAGTGGGCCACCACCATCCTGGACATTGAGCGCTCCTTC
CCCGTATTCCTGAGGAAGGCCTTCCGCTCTGGGGAGATGGTCACCGTGGGC
AAGAGCTCGGACGGCACTCCTGACCGCAGGTGGTGCTTCAGGGTGGATGAG
GTGAACTGGTCTCACTGGAACCAGAACTTGGGCATCATCAACGAGGACCCG
GGCAAGAATGAGACCTACCAGTATTATGCTTCTCGCATACCGTGGGCCGC
CTCCGCAGGGATCGCTGGTCCTCGGTGGTACCCCGCGTGGTGGAACTGAAC
AAGAACTCGAACCCGGACGAGGTGGTGGTGCCTCTGGACAGCATGGGGAAC
CCCCGCTGCGATGGCCACCAGCAGGGTTACCCCCGCAAGTGGAGGACTGAT
GACGCCCCGCTCTAG
```

FIG. 2A

SEQ.ID.NO.6.
The nucleotide sequence of human VR3A+B- is shown
including 337 bp 5' UT and 547 bp 3'UT.

CAATTGGGATTTAAACCCAGGGACTATCCAGCCCCAAAGCCCTTCCCACCAC
ACCAGGTGGCCTGTCCTGGGGCCAGCTCTGCACACAGGGCCTGGTGCCCCCG
GGGTGCTTGGGAAGTGGCAGGGCAGAGGTGGGCCCTGTGGCTGTTCTGGCTC
AGCTTCTAAAACAAGAGCCTCTGCTGGGGGCAGAGGGGCCGTGAACCCCTGA
AATGTTAGGCAGATACCCTGTGGGAGCTTTGTTCTGGATGCTAAGAACCGC
TTGAGGATTTAAGCTTTGCCACTTTGGCTCCGGAGCAAGGGCAGAGGCTGAG
CAGTGCAGACGGGCCTGGGGCAGGCATGGCGGATTCCAGCGAAGGCCCCGC
GCGGGGCCCGGGGAGGTGGCTGAGCTCCCCGGGGATGAGAGTGGCACCCCAG
GTGGGGAGGCTTTTCCTCTCTCCTCCCTGGCCAATCTGTTTGAGGGGGAGGA
TGGCTCCCTTTCGCCCTCACCGGCTGATGCCAGTCGCCCTGCTGGCCCAGGC
GATGGGCGACCAAATCTGCGCATGAAGTTCCAGGGCGCCTTCCGCAAGGGGG
TGCCCAACCCCATCGATCTGCTGGAGTCCACCCTATATGAGTCCTCGGTGGT
GCCTGGGCCCAAGAAAGCACCCATGGACTCACTGTTTGACTACGGCACCTAT
CGTCACCACTCCAGTGACAACAAGAGGTGGAGGAAGAAGATCATAGAGAAGC
AGCCGCAGAGCCCCAAAGCCCCTGCCCCTCAGCCGCCCCCCATCCTCAAAGT
CTTCAACCGGCCTATCCTCTTTGACATCGTGTCCCGGGGCTCCACTGCTGAC
CTGGACGGGCTGCTCCCATTCTTGCTGACCCACAAGAAACGCCTAACTGATG
AGGAGTTTCGAGAGCCATCTACGGGGAAGACCTGCCTGCCCAAGGCCTTGCT
GAACCTGAGCAATGGCCGCAACGACACCATCCCTGTGCTGCTGGACATCGCG
GAGCGCACCGGCAACATGCGGGAGTTCATTAACTCGCCCTTCCGTGACATCT
ACTATCGAGGTCAGACAGCCCTGCACATCGCCATTGAGCGTCGCTGCAAACA
CTACGTGGAACTTCTCGTGGCCCAGGGAGCTGATGTCCACGCCCAGGCCCGT
GGGCGCTTCTTCCAGCCCAAGGATGAGGGGGGCTACTTCTACTTTGGGGAGC
TGCCCCTGTCGCTGGCTGCCTGCACCAACCAGCCCCACATTGTCAACTACCT
GACGGAGAACCCCCACAAGAAGGCGGACATGCGGCGCCAGGACTCGCGAGGC
AACACAGTGCTGCATGCGCTGGTGGCCATTGCTGACAACACCCGTGAGAACA
CCAAGTTTGTTACCAAGATGTACGACCTGCTGCTGCTCAAGTGTGCCCGCCT
CTTCCCCGACAGCAACCTGGAGGCCGTGCTCAACAACGACGGCCTCTCGCCC
CTCATGATGGCTGCCAAGACGGGCAAGATTGGGATCTTTCAGCACATCATCC
GGCGGGAGGTGACGGATGAGGACACACGGCACCTGTCCCGCAAGTTCAAGGA
CTGGGCCTATGGGCCAGTGTATTCCTCGCTTTATGACCTCTCCTCCCTGGAC
ACGTGTGGGGAAGAGGCCTCCGTGCTGGAGATCCTGGTGTACAACAGCAAGA
TTGAGAACCGCCACGAGATGCTGGCTGTGGAGCCCATCAATGAACTGCTGCG
GGACAAGTGGCGCAAGTTCGGGGCCGTCTCCTTCTACATCAACGTGGTCTCC
TACCTGTGTGCCATGGTCATCTTCACTCTCACCGCCTACTACCAGCCGCTGG
AGGGCACACCGCCGTACCCTTACCGCACCACGGTGGACTACCTGCGGCTGGC

FIG. 2B

```
TGGCGAGGTCATTACGCTCTTCACTGGGGTCCTGTTCTTCATCACCAACATC
AAAGACTTGTTCATGAAGAAATGCCCTGGAGTGAATTCTCTCTTCATTGATG
GCTCCTTCCAGCTGCTCTACTTCATCTACTCTGTCCTGGTGATCGTCTCAGC
AGCCCTCTACCTGGCAGGGATCGAGGCCTACCTGGCCGTGATGGTCTTTGCC
CTGGTCCTGGGCTGGATGAATGCCCTTTACTTCACCCGTGGGCTGAAGCTGA
CGGGGACCTATAGCATCATGATCCAGAAGATTCTCTTCAAGGACCTTTTCCG
ATTCCTGCTCGTCTACTTGCTCTTCATGATCGGCTACGCTTCAGCCCTGGTC
TCCCTCCTGAACCCGTGTGCCAACATGAAGGTGTGCAATGAGGACCAGACCA
ACTGCACAGTGCCCACTTACCCCTCGTGCCGTGACAGCGAGACCTTCAGCAC
CTTCCTCCTGGACCTGTTTAAGCTGACCATCGGCATGGGCGACCTGGAGATG
CTGAGCAGCACCAAGTACCCCGTGGTCTTCATCATCCTGCTGGTGACCTACA
TCATCCTCACCTTTGTGCTGCTCCTCAACATGCTCATTGCCCTCATGGGCGA
GACAGTGGGCCAGGTCTCCAAGGAGAGCAAGCACATCTGGAAGCTGCAGTGG
GCCACCACCATCCTGGACATTGAGCGCTCCTTCCCCGTATTCCTGAGGAAGG
CCTTCCGCTCTGGGGAGATGGTCACCGTGGGCAAGAGCTCGGACGGCACTCC
TGACCGCAGGTGGTGCTTCAGGGTGGATGAGGTGAACTGGTCTCACTGGAAC
CAGAACTTGGGCATCATCAACGAGGACCCGGGCAAGAATGAGACCTACCAGT
ATTATGGCTTCTCGCATACCGTGGGCCGCCTCCGCAGGGATCGCTGGTCCTC
GGTGGTACCCCGCGTGGTGGAACTGAACAAGAACTCGAACCCGGACGAGGTG
GTGGTGCCTCTGGACAGCATGGGGAACCCCCGCTGCGATGGCCACCAGCAGG
GTTACCCCCGCAAGTGGAGGACTGATGACGCCCCGCTCTAGGGACTGCAGCC
CAGCCCCAGCTTCTCTGCCCACTCATTTCTAGTCCAGCCGCATTTCAGCAGT
GCCTTCTGGGGTGTCCCCCCACACCCTGCTTTGGCCCCAGAGGCGAGGGACC
AGTGGAGGTGCCAGGGAGGCCCCAGGACCCTGTGGTCCCCTGGCTCTGCCTC
CCCACCCTGGGGTGGGGGCTCCCGGCCACCTGTCTTGCTCCTATGGAGTCAC
ATAAGCCAACGCCAGAGCCCCTCCACCTCAGGCCCCAGCCCCTGCCTCTCCA
TTATTTATTTGCTCTGCTCTCAGGAAGCGACGTGACCCCTGCCCCAGCTGGA
ACCTGGCAGAGGCCTTAGGACCCCGTTCCAAGTGCACTGCCCGGCCAAGCCC
CAGCCTCAGCCTGCGCCTGAGCTGCATGCGCCACCATTTTTGGCAGCGTGGC
AGCTTTGCAAGGGGCTGGGGCCCTCGGCGTGGGGCCATGCCTTCTGTGTGTT
CTGTAGTGTCTGGGATTTGCCGGTGCTCAATAAATGTTTATTCATTGACGGT
GGAAAAAAAAAAAAAA
```

FIG. 3

SEQ.ID.NO.7.
Coding sequence for human VR3A+B-   (871 amino acids)

MADSSEGPRAGPGEVAELPGDESGTPGGEAFPLSSLANLFEGEDGSLSPSP
ADASRPAGPGDGRPNLRMKFQGAFRKGVPNPIDLLESTLYESSVVPGPKKA
PMDSLFDYGTYRHHSSDNKRWRKKIIEKQPQSPKAPAPQPPPILKVFNRPI
LFDIVSRGSTADLDGLLPFLLTHKKRLTDEEFREPSTGKTCLPKALLNLSN
GRNDTIPVLLDIAERTGNMREFINSPFRDIYYRGQTALHIAIERRCKHYVE
LLVAQGADVHAQARGRFFQPKDEGGYYFGELPLSLAACTNQPHIVNYLTE
NPHKKADMRRQDSRGNTVLHALVAIADNTRENTKFVTKMYDLLLLKCARLF
PDSNLEAVLNNDGLSPLMMAAKTGKIGIFQHIIRREVTDEDTRHLSRKFKD
WAYGPVYSSLYDLSSLDTCGEEASVLEILVYNSKIENRHEMLAVEPINELL
RDKWRKFGAVSFYINVVSYLCAMVIFTLTAYYQPLEGTPPYPYRTTVDYLR
LAGEVITLFTGVLFFITNIKDLFMKKCPGVNSLFIDGSFQLLYFIYSVLVI
VSAALYLAGIEAYLAVMVFALVLGWMNALYFTRGLKLTGTYSIMIQKILFK
DLFRFLLVYLLFMIGYASALVSLLNPCANMKVCNEDQTNCTVPTYPSCRDS
ETFSTFLLDLFKLTIGMGDLEMLSSTKYPV*VFIILLVTYIILTFVLLLNML*
*IALMGETVGQVSKESKHIWKLQWATTILDIERSFPVFLRKAFRSGEMVTVG*
*KSSDGTPDRRWCFRVDEVNWSHWNQNLGIINEDPGKNETYQYYGFSHTVGR*
*LRRDRWSSVVPRVVELNKNSNPDEVVVPLDSMGNPRCDGHQQGYPRKWRTDDAPL*

FIG. 4A

SEQ.ID.NO.8.
Human VR3A-B- nucleotide sequence of the coding sequence (2436 bp).

```
ATGGCGGATTCCAGCGAAGGCCCCCGCGCGGGGCCCGGGGAGGTGGCTGAG
CTCCCCGGGGATGAGAGTGGCACCCCAGGTGGGGAGGCTTTTCCTCTCTCC
TCCCTGGCCAATCTGTTTGAGGGGGAGGATGGCTCCCTTTCGCCCTCACCG
GCTGATGCCAGTCGCCCTGCTGGCCCAGGCGATGGGCGACCAAATCTGCGC
ATGAAGTTCCAGGGCGCCTTCCGCAAGGGGGTGCCCAACCCCATCGATCTG
CTGGAGTCCACCCTATATGAGTCCTCGGTGGTGCCTGGGCCAAGAAAGCA
CCCATGGACTCACTGTTTGACTACGGCACCTATCGTCACCACTCCAGTGAC
AACAAGAGGTGGAGGAAGAAGATCATAGAGAAGCAGCCGCAGAGCCCCAAA
GCCCCTGCCCCTCAGCCGCCCCCCATCCTCAAAGTCTTCAACCGGCCTATC
CTCTTTGACATCGTGTCCCGGGGCTCCACTGCTGACCTGGACGGGCTGCTC
CCATTCTTGCTGACCCACAAGAAACGCCTAACTGATGAGGAGTTTCGAGAG
CCATCTACGGGGAAGACCTGCCTGCCCAAGGCCTTGCTGAACCTGAGCAAT
GGCCGCAACGACACCATCCCTGTGCTGCTGGACATCGCGGAGCGCACCGGC
AACATGCGGGAGTTCATTAACTCGCCCTTCCGTGACATCTACTATCGAGGT
CAGACAGCCCTGCACATCGCCATTGAGCGTCGCTGCAAACACTACGTGGAA
CTTCTCGTGGCCCAGGGAGCTGATGTCCACGCCCAGGCCCGTGGGCGCTTC
TTCCAGCCCAAGGATGAGGGGGGCTACTTCTACTTTGGGGAGCTGCCCCTG
TCGCTGGCTGCCTGCACCAACCAGCCCCACATTGTCAACTACCTGACGGAG
AACCCCCACAAGAAGGCGGACATGCGGCGCCAGGACTCGCGAGGCAACACA
GTGCTGCATGCGCTGGTGGCCATTGCTGACAACACCCGTGAGAACACCAAG
TTTGTTACCAAGATGTACGACCTGCTGCTGCTCAAGTGTGCCCGCCTCTTC
CCCGACAGCAACCTGGAGGCCGTGCTCAACAACGACGGCCTCTCGCCCCTC
ATGATGGCTGCCAAGACGGGCAAGATTGAGAACCGCCACGAGATGCTGGCT
GTGGAGCCCATCAATGAACTGCTGCGGGACAAGTGGCGCAAGTTCGGGGCC
GTCTCCTTCTACATCAACGTGGTCTCCTACCTGTGTGCCATGGTCATCTTC
ACTCTCACCGCCTACTACCAGCCGCTGGAGGGCACACCGCCGTACCCTTAC
CGCACCACGGTGGACTACCTGCGGCTGGCTGGCGAGGTCATTACGCTCTTC
ACTGGGGTCCTGTTCTTCATCACCAACATCAAAGACTTGTTCATGAAGAAA
TGCCCTGGAGTGAATTCTCTCTTCATTGATGGCTCCTTCCAGCTGCTCTAC
TTCATCTACTCTGTCCTGGTGATCGTCTCAGCAGCCCTCTACCTGGCAGGG
ATCGAGGCCTACCTGGCCGTGATGGTCTTTGCCCTGGTCCTGGGCTGGATG
AATGCCCTTTACTTCACCCGTGGGCTGAAGCTGACGGGGACCTATAGCATC
```

FIG. 4B

```
ATGATCCAGAAGATTCTCTTCAAGGACCTTTTCCGATTCCTGCTCGTCTAC
TTGCTCTTCATGATCGGCTACGCTTCAGCCCTGGTCTCCCTCCTGAACCCG
TGTGCCAACATGAAGGTGTGCAATGAGGACCAGACCAACTGCACAGTGCCC
ACTTACCCCTCGTGCCGTGACAGCGAGACCTTCAGCACCTTCCTCCTGGAC
CTGTTTAAGCTGACCATCGGCATGGGCGACCTGGAGATGCTGAGCAGCACC
AAGTACCCCGTGGTCTTCATCATCCTGCTGGTGACCTACATCATCCTCACC
TTTGTGCTGCTCCTCAACATGCTCATTGCCCTCATGGGCGAGACAGTGGGC
CAGGTCTCCAAGGAGAGCAAGCACATCTGGAAGCTGCAGTGGGCCACCACC
ATCCTGGACATTGAGCGCTCCTTCCCCGTATTCCTGAGGAAGGCCTTCCGC
TCTGGGGAGATGGTCACCGTGGGCAAGAGCTCGGACGGCACTCCTGACCGC
AGGTGGTGCTTCAGGGTGGATGAGGTGAACTGGTCTCACTGGAACCAGAAC
TTGGGCATCATCAACGAGGACCCGGGCAAGAATGAGACCTACCAGTATTAT
GGCTTCTCGCATACCGTGGGCCGCCTCCGCAGGGATCGCTGGTCCTCGGTG
GTACCCCGCGTGGTGGAACTGAACAAGAACTCGAACCCGGACGAGGTGGTG
GTGCCTCTGGACAGCATGGGGAACCCCCGCTGCGATGGCCACCAGCAGGGT
TACCCCCGCAAGTGGAGGACTGATGACGCCCCGCTCTAG
```

FIG. 5

SEQ.ID.NO.9.
Coding sequence for human VR3A-B- (811 amino acids)

MADSSEGPRAGPGEVAELPGDESGTPGGEAFPLSSLANLFEGEDGSLSPSP
ADASRPAGPGDGRPNLRMKFQGAFRKGVPNPIDLLESTLYESSVVPGPKKA
PMDSLFDYGTYRHHSSDNKRWRKKIIEKQPQSPKAPAPQPPPILKVFNRPI
LFDIVSRGSTADLDGLLPFLLTHKKRLTDEEFREPSTGKTCLPKALLNLSN
GRNDTIPVLLDIAERTGNMREFINSPFRDIYYRGQTALHIAIERRCKHYVE
LLVAQGADVHAQARGRFFQPKDEGGYFYFGELPLSLAACTNQPHIVNYLTE
NPHKKADMRRQDSRGNTVLHALVAIADNTRENTKFVTKMYDLLLLKCARLF
PDSNLEAVLNNDGLSPLMMAAKTGKIENRHEMLAVEPINELLRDKWRKFGA
VSFYINVVSYLCAMVIFTLTAYYQPLEGTPPYPYRTTVDYLRLAGEVITLF
TGVLFFITNIKDLFMKKCPGVNSLFIDGSFQLLYFIYSVLVIVSAALYLAG
IEAYLAVMVFALVLGWMNALYFTRGLKLTGTYSIMIQKILFKDLFRFLLVY
LLFMIGYASALVSLLNPCANMKVCNEDQTNCTVPTYPSCRDSETFSTFLLD
LFKLTIGMGDLEMLSSTKYPVVFIILLVTYIILTFVLLLNMLIALMGETVG
QVSKESKHIWKLQWATTILDIERSFPVFLRKAFRSGEMTVGKSSDGTPDR
RWCFRVDEVNWSHWNQNLGIINEDPGKNETYQYYGFSHTVGRLRRDRWSSV
VPRVVELNKNSNPDEVVVPLDSMGNPRCDGHQQGYPRKWRTDDAPL

FIG. 6

SEQ.ID.NO.10.
Human VR3A+B+ nucleotide sequence of the coding sequence (2229 bp).

ATGGCGGATTCCAGCGAAGGCCCCCGCGCGGGGCCCGGGGAGGTGGCTGAGCT
CCCCGGGGATGAGAGTGGCACCCCAGGTGGGGAGGCTTTTCCTCTCTCCTCCC
TGGCCAATCTGTTTGAGGGGGAGGATGGCTCCCTTTCGCCCTCACCGGCTGAT
GCCAGTCGCCCTGCTGGCCCAGGCGATGGGCGACCAAATCTGCGCATGAAGTT
CCAGGGCGCCTTCCGCAAGGGGGTGCCCAACCCCATCGATCTGCTGGAGTCCA
CCCTATATGAGTCCTCGGTGGTGCCTGGGCCCAAGAAAGCACCCATGGACTCA
CTGTTTGACTACGGCACCTATCGTCACCACTCCAGTGACAACAAGAGGTGGAG
GAAGAAGATCATAGAGAAGCAGCCGCAGAGCCCCAAAGCCCTGCCCCTCAGC
CGCCCCCCATCCTCAAAGTCTTCAACCGGCCTATCCTCTTTGACATCGTGTCC
CGGGGCTCCACTGCTGACCTGGACGGGCTGCTCCCATTCTTGCTGACCCACAA
GAAACGCCTAACTGATGAGGAGTTTCGAGAGCCATCTACGGGGAAGACCTGCC
TGCCCAAGGCCTTGCTGAACCTGAGCAATGGCCGCAACGACACCATCCCTGTG
CTGCTGGACATCGCGGAGCGCACCGGCAACATGAGGGAGTTCATTAACTCGCC
CTTCCGTGACATCTACTATCGAGGTCAGACAGCCCTGCACATCGCCATTGAGC
GTCGCTGCAAACACTACGTGGAACTTCTCGTGGCCCAGGGAGCTGATGTCCAC
GCCCAGGCCCGTGGGCGCTTCTTCCAGCCCAAGGATGAGGGGGGCTACTTCTA
CTTTGGGGAGCTGCCCCTGTCGCTGGCTGCCTGCACCAACCAGCCCCACATTG
TCAACTACCTGACGGAGAACCCCCACAAGAAGGCGGACATGCGGCGCCAGGAC
TCGCGAGGCAACACAGTGCTGCATGCGCTGGTGGCCATTGCTGACAACACCCG
TGAGAACACCAAGTTTGTTACCAAGATGTACGACCTGCTGCTGCTCAAGTGTG
CCCGCCTCTTCCCCGACAGCAACCTGGAGGCCGTGCTCAACAACGACGGCCTC
TCGCCCCTCATGATGGCTGCCAAGACGGGCAAGATTGGGATCTTTCAGCACAT
CATCCGGCGGGAGGTGACGGATGAGGACACACGGCACCTGTCCCGCAAGTTCA
AGGACTGGGCCTATGGGCCAGTGTATTCCTCGCTTTATGACCTCTCCTCCCTG
GACACGTGTGGGGAAGAGGCCTCCGTGCTGGAGATCCTGGTGTACAACAGCAA
GATTGAGAACCGCCACGAGATGCTGGCTGTGGAGCCCATCAATGAACTGCTGC
GGGACAAGTGGCGCAAGTTCGGGGCCGTCTCCTTCTACATCAACGTGGTCTCC
TACCTGTGTGCCATGGTCATCTTCACTCTCACCGCCTACTACCAGCCGCTGGA
GGGCACACCGCCGTACCCTTACCGCACCACGGTGGACTACCTGCGGCTGGCTG
GCGAGGTCATTACGCTCTTCACTGGGGTCCTGTTCTTCTTCACCAACATCAAA
GACTTGTTCATGAAGAAATGCCCTGGAGTGAATTCTCTCTTCATTGATGGCTC
CTTCCAGCTGCTCTACTTCATCTACTCTGTCCTGGTGATCGTCTCAGCAGCCC
TCTACCTGGCAGGGATCGAGGCCTACCTGGCCGTGATGGTCTTTGCCCTGGTC
CTGGGCTGGATGAATGCCCTTTACTTCACCCGTGGGCTGAAGCTGACGGGGAC
CTATAGCATCATGATCCAGA<u>AGAT</u>TCTCTTCAAGGACCTTTTCCGATTCCTGC
TCGTCTACTTGCTCTTCATGATCGGCTACGCTTCAGCCCTGGTCTCCCTCCTG
AACCCGTGTGCCAACATGAAGGTGTGCAATGAGGACCAGACCAACTGCACAGT
GCCCACTTACCCCTCGTGCCGTGACAGCGAGACCTTCAGCACCTTCCTCCTGG
ACCTGTTTAAGCTGACCATCGGCATGGGCGACCTGGAGATGCTGAGCAGCACC
AAGTACCCCGTGGTCTTCATCATCCTGCTGGTGACCTACATCATCCTCACCTT
TGTGCTGCTCCTCAACATGCTCATTGCCCTCATGGGCGAGACAGTGGGCCAGG
TCTCCAAGGAGAGCAAGCACATCTGGAAGCTGCAGAGCGGCAGGCGCAGGCTGTGA

FIG. 7A

SEQ.ID.NO.11.
The nucleotide sequence of human VR3A+B+ is shown including 836 bp 5' UT and 994 bp 3'UT.

```
TGTGCAGGCCAGGGAGGGCTTTCCAGAGGAGCCCAGTTGAGCTGGAACACCA
GTGGGGAGGAGTTGACCAGCAAAGGTGCAGGGAGGGATCAGCACTTTGCACT
GGGGAGCAGAGTTTGTGCACTGGGGAAGTCAACTCAAGTATTGGAGCCTCAG
TTTCCTGTTCTGTAAAATGGGTTCATCATGACAGTGTTTGATGAGGAAAAGG
ACTGCCGGCCTACACAGCAAGTCCACATGGATTTTCTGAGCCCCTCCTGTGC
CTGAAGCCCACGGTTAATGGTTCTGCCTTAGCAGGTGCTTACCACGTGCCAG
GCACTGCACTGCACTGGCCACTGGACTGCATGTTCTGTCCATGAGGCTTGA
TATCCCCATCTTACAGATCAGGAAGCTGAGGCTATGAAATGTCGACTTGCTC
AATGTCATGGAATGACTAAGTGTGGAGCCTGGATTTGAACTTGGCTCTCTGG
GGCTCCAAAGCTGGCTTTCTTGGTCAGCAGTAGGGTCTGGGATCCAAGTATG
GGGTCCCAGCTTGACCCTGAAGTCCACCCTCTTTCAGCTAATGCCCAAGGTA
GTTGGACCTGGGGCCAATTTGTGTTTCCAGGTTCGTGAAAGAGCTCCTGTTG
CAGTTCCCGCCTGAGGCTTGGCGGCCAACCACATCTGGGAGTGGCCTCCCTG
TGCCCCTGTCATTACAACGGTGGCTTTGAAGCAGCTGGCAGCACTGCTGCTT
GTCCACGTGGAAGGGGGCTTCCTGGAGCCCCGCCCTGGCCGGGTTCTGCC
TGACTCCCCTTTCATTCCCTTGCAGGCTGAGCAGTGCAGACGGGCCTGGGGC
AGGCATGGCGGATTCCAGCGAAGGCCCCGCGCGGGGCCCGGGGAGGTGGCT
GAGCTCCCCGGGGATGAGAGTGGCACCCCAGGTGGGGAGGCTTTTCCTCTCT
CCTCCCTGGCCAATCTGTTTGAGGGGGAGGATGGCTCCCTTTCGCCCTCACC
GGCTGATGCCAGTCGCCCTGCTGGCCCAGGCGATGGGCGACCAAATCTGCGC
ATGAAGTTCCAGGGCGCCTTCCGCAAGGGGGTGCCCAACCCCATCGATCTGC
TGGAGTCCACCCTATATGAGTCCTCGGTGGTGCCTGGGCCCAAGAAAGCACC
CATGGACTCACTGTTTGACTACGGCACCTATCGTCACCACTCCAGTGACAAC
AAGAGGTGGAGGAAGAAGATCATAGAGAAGCAGCCGCAGAGCCCCAAAGCCC
CTGCCCCTCAGCCGCCCCCATCCTCAAAGTCTTCAACCGGCCTATCCTCTT
TGACATCGTGTCCCGGGGCTCCACTGCTGACCTGGACGGGCTGCTCCCATTC
TTGCTGACCCACAAGAAACGCCTAACTGATGAGGAGTTTCGAGAGCCATCTA
CGGGGAAGACCTGCCTGCCCAAGGCCTTGCTGAACCTGAGCAATGGCCGCAA
CGACACCATCCCTGTGCTGCTGGACATCGCGGAGCGCACCGGCAACATGAGG
GAGTTCATTAACTCGCCCTTCCGTGACATCTACTATCGAGGTCAGACAGCCC
TGCACATCGCCATTGAGCGTCGCTGCAAACACTACGTGGAACTTCTCGTGGC
CCAGGGAGCTGATGTCCACGCCCAGGCCCGTGGGCGCTTCTTCCAGCCCAAG
GATGAGGGGGGCTACTTCTACTTTGGGGAGCTGCCCCTGTCGCTGGCTGCCT
GCACCAACCAGCCCCACATTGTCAACTACCTGACGGAGAACCCCCACAAGAA
GGCGGACATGCGGCGCCAGGACTCGCGAGGCAACACAGTGCTGCATGCGCTG
GTGGCCATTGCTGACAACACCCGTGAGAACACCAAGTTTGTTACCAAGATGT
ACGACCTGCTGCTGCTCAAGTGTGCCCGCCTCTTCCCCGACAGCAACCTGGA
GGCCGTGCTCAACAACGACGGCCTCTCGCCCCTCATGATGGCTGCCAAGACG
GGCAAGATTGGGATCTTTCAGCACATCATCCGGCGGGAGGTGACGGATGAGG
ACACACGGCACCTGTCCCGCAAGTTCAAGGACTGGGCCTATGGGCCAGTGTA
TTCCTCGCTTTATGACCTCTCCTCCCTGGACACGTGTGGGGAAGAGGCCTCC
GTGCTGGAGATCCTGGTGTACAACAGCAAGATTGAGAACCGCCACGAGATGC
TGGCTGTGGAGCCCATCAATGAACTGCTGCGGGACAAGTGGCGCAAGTTCGG
```

FIG. 7B

```
GGCCGTCTCCTTCTACATCAACGTGGTCTCCTACCTGTGTGCCATGGTCAT
CTTCACTCTCACCGCCTACTACCAGCCGCTGGAGGGCACACCGCCGTACCC
TTACCGCACCACGGTGGACTACCTGCGGCTGGCTGGCGAGGTCATTACGCT
CTTCACTGGGGTCCTGTTCTTCTTCACCAACATCAAAGACTTGTTCATGAA
GAAATGCCCTGGAGTGAATTCTCTCTTCATTGATGGCTCCTTCCAGCTGCT
CTACTTCATCTACTCTGTCCTGGTGATCGTCTCAGCAGCCCTCTACCTGGC
AGGGATCGAGGCCTACCTGGCCGTGATGGTCTTTGCCCTGGTCCTGGGCTG
GATGAATGCCCTTTACTTCACCCGTGGGCTGAAGCTGACGGGGACCTATAG
CATCATGATCCAGAAGATTCTCTTCAAGGACCTTTTCCGATTCCTGCTCGT
CTACTTGCTCTTCATGATCGGCTACGCTTCAGCCCTGGTCTCCCTCCTGAA
CCCGTGTGCCAACATGAAGGTGTGCAATGAGGACCAGACCAACTGCACAGT
GCCCACTTACCCCTCGTGCCGTGACAGCGAGACCTTCAGCACCTTCCTCCT
GGACCTGTTTAAGCTGACCATCGGCATGGGCGACCTGGAGATGCTGAGCAG
CACCAAGTACCCCGTGGTCTTCATCATCCTGCTGGTGACCTACATCATCCT
CACCTTTGTGCTGCTCCTCAACATGCTCATTGCCCTCATGGGCGAGACAGT
GGGCCAGGTCTCCAAGGAGAGCAAGCACATCTGGAAGCTGCAGAGCGGCAG
GCGCAGGCTGTGAGGCTCACCGATGTCCCTCCTGACCCTCCCTCCCCGCAG
TGGGCCACCACCATCCTGGACATTGAGCGCTCCTTCCCCGTATTCCTGAGG
AAGGCCTTCCGCTCTGGGGAGATGGTCACCGTGGGCAAGAGCTCGGACGGC
ACTCCTGACCGCAGGTGGTGCTTCAGGGTGGATGAGGTGAACTGGTCTCAC
TGGAACCAGAACTTGGGCATCATCAACGAGGACCCGGGCAAGAATGAGACC
TACCAGTATTATGGCTTCTCGCATACCGTGGGCCGCCTCCGCAGGGATCGC
TGGTCCTCGGTGGTACCCCGCGTGGTGGAACTGAACAAGAACTCGAACCCG
GACGAGGTGGTGGTGCCTCTGGACAGCATGGGGAACCCCCGCTGCGATGGC
CACCAGCAGGGTTACCCCGCAAGTGGAGGACTGATGACGCCCGCTCTAG
GGACTGCAGCCCAGCCCCAGCTTCTCTGCCCACTCATTTCTAGTCCAGCCG
CATTTCAGCAGTGCCTTCTGGGGTGTCCCCCCACACCCTGCTTTGGCCCCA
GAGGCGAGGGACCAGTGGAGGTGCCAGGGAGGCCCCAGGACCCTGTGGTCC
CCTGGCTCTGCCTCCCCACCCTGGGGTGGGGGCTCCCGGCCACCTGTCTTG
CTCCTATGGAGTCACATAAGCCAACGCCAGAGCCCCTCCACCTCAGGCCCC
AGCCCCTGCCTCTCCATTATTTATTTGCTCTGCTCTCAGGAAGCGACGTGA
CCCCTGCCCCAGCTGGAACCTGGCAGAGGCCTTAGGACCCCGTTCCAAGTG
CACTGCCCGGCCAAGCCCCAGCCTCAGCCTGCGCCTGAGCTGCATGCGCCA
CCATTTTTGGCAGCGTGGCAGCTTTGCAAGGGGCTGGGGCCCTCGGCGTGG
GGCCATGCCTTCTGTGTGTTCTGTAGTGTCTGGGATTTGCCGGTGCTCAAT
AAATGTTTATTCATTGACGGTGGAAAAAAAAAAAAAA
```

FIG. 8

SEQ.ID.NO.12.
Coding sequence for human VR3A+B+ (742 amino acids)

MADSSEGPRAGPGEVAELPGDESGTPGGEAFPLSSLANLFEGEDGSLSPS
PADASRPAGPGDGRPNLRMKFQGAFRKGVPNPIDLLESTLYESSVVPGPK
KAPMDSLFDYGTYRHHSSDNKRWRKKIIEKQPQSPKAPAPQPPPILKVFN
RPILFDIVSRGSTADLDGLLPFLLTHKKRLTDEEFREPSTGKTCLPKALL
NLSNGRNDTIPVLLDIAERTGNMREFINSPFRDIYYRGQTALHIAIERRC
KHYVELLVAQGADVHAQARGRFFQPKDEGGYFYFGELPLSLAACTNQPHI
VNYLTENPHKKADMRRQDSRGNTVLHALVAIADNTRENTKFVTKMYDLLL
LKCARLFPDSNLEAVLNNDGLSPLMMAAKTGKIGIFQHIIRREVTDEDTR
HLSRKFKDWAYGPVYSSLYDLSSLDTCGEEASVLEILVYNSKIENRHEML
AVEPINELLRDKWRKFGAVSFYINVVSYLCAMVIFTLTAYYQPLEGTPPY
PYRTTVDYLRLAGEVITLFTGVLFFFTNIKDLFMKKCPGVNSLFIDGSFQ
LLYFIYSVLVIVSAALYLAGIEAYLAVMVFALVLGWMNALYFTRGLKLTG
TYSIMIQKILFKDLFRFLLVYLLFMIGYASALVSLLNPCANMKVCNEDQT
NCTVPTYPSCRDSETFSTFLLDLFKLTIGMGDLEMLSSTKYPVVFIILLV
TYIILTFVLLLNMLIALMGETVGQVSKESKHIWKLQSGRRRL

FIG. 9

| | Water-injected controls | VR3 A+B- | VR3 A-B- | VR3 A+B+ |
|---|---|---|---|---|
| Number of living oocytes | 88 | 9 | 47 | 29 |
| Number of dead oocytes | 44 | 90 | 40 | 54 |
| Percent Alive | 67% | 9% (* p<e-17) | 54% (p = 0.99) | 35% (* p = 5.4 e-6) |

VRI and water

VRI and VR3 A⁺B⁻

VR1 and water

VR1 and VR3 A+B−

FIG. 13

| Tissue or cell type | hVR3 (mean intensity) | hVR1 (mean intensity) |
| --- | --- | --- |
| Liver | 900+/-50 (p<0.005) | 55+/-3 (p<0.05) |
| Raji lymphoma cell line | 255+/-20 (p<0.005) | NS |
| Spleen | 196+/-19 (p<0.01) | NS |
| Lung | 150+/-22 (p<0.01) | NS |
| DRG | 129+/-21 (p<0.025) | 90+/-3 (p<0.05) |
| Ovary | 128+/-9 (p<0.0025) | 69+/-2 (p<0.0005) |
| Placenta | 120+/-7 (p<0.001) | NS |
| Trachea | 106+/-7 (p<0.001) | 54+/-4 (p<0.01) |
| Small intestine | 105+/-3 (p<0.001) | 62+/-5 (p<0.01) |
| Prostate* | 72+/-5 (p<0.0025) | 38+/-1 (p<0.0005) |
| Kidney | 62+/-4 (p<0.05) | 57+/-4 (p<0.005) |
| Spinal cord | 57+/-2 (p<0.00025) | 47+/-3 (p<0.005) |

Values are the mean intensity of the labeled cRNA hybridizing to the cDNA microarray +/- S.E.M. The mean intensity for cRNAs from all tissues shown were significantly different (p value in the parentheses) from 75% of the control plant cDNA value. Data are averaged from 3-6 experiments. NS: not significantly different form plant gene control (see Luo et al., 1999 for more detailed methods). *Tissue from which the VR3 was cloned.

DNA ENCODING HUMAN VANILLOID RECEPTOR VR3

BACKGROUND OF THE INVENTION

Noxious chemical, thermal and mechanical stimuli excite peripheral nerve endings of small diameter sensory neurons (nociceptors) in sensory ganglia (e.g., dorsal root, nodose and trigeminal ganglia) and initiate signals that are perceived as pain. These neurons are crucial for the detection of harmful or potentially harmful stimuli (heat) and tissue damage ($H^+$ (local tissue acidosis), and/or stretch) which arise from changes in the extracellular space during inflammatory or ischaemic conditions (Wall and Melzack, 1994). The vanilloid capsaicin (8-methyl-N-vanillyl-6-nonenamide), the main pungent ingredient in "hot" capsicum peppers, is a very selective activator of thinly or unmyelinated nociceptive afferents (Szolcsanyi, 1993; Szolcsanyi, 1996). Electrophysiological studies have shown that vanilloids excite small sensory neurons by activating a plasma membrane channel that is non-selectively permeable to cations (Bevan and Szolcsanyi, 1990; Oh et al., 1996; Wood et al., 1988). The ultra potent tricyclic diterpene resiniferatoxin from Euphorbia plants (RTX; (Szolcsanyi et al., 1991)) binds with nanomolar affinity at the capsaicin binding site and has revealed a very localized distribution of capsaicin receptors to rat somatic and visceral primary sensory neurons (Szallasi, 1995).

The vanilloid receptor VR1 (Caterina et al., 1997) is thought to be a heat-sensing receptor whose threshold is decreased in the presence of protons or capsaicin (Tominaga et al., 1998). Capsaicin and protons interact at specific membrane recognition sites (vanilloid receptors) expressed almost exclusively by primary sensory neurons involved in nociception and neurogenic inflammation (Bevan and Szolcsanyi, 1990). The vanilloid ("capsaicin") receptor VR1 is activated by capsaicin and RTX, and activation of VR1 is blocked by the antagonists capsazepine (CPZ; (Bevan et al., 1992)) and ruthenium red (RR; (Caterina et al., 1997; Wood et al., 1988)).

Hydropathicity analysis of the amino acid sequence of VR1 reveals 6 potential membrane spanning regions (S1–S6) and a putative pore-loop region between S5 and S6. A large intracellular domain contains 3 ankyrin repeat domains. (Caterina et al., 1997). This channel has significant structural similarities with the putative "store-operated" TRP calcium channel family. VR1 is a ligand-gated non-selective cation channel that shows pronounced outward rectification (Caterina et al., 1997). Importantly, VR1 is highly permeable to Ca2+, an ion known to be very important in regulating cell function ((Blackstone and Sheng, 1999; Gupta and Pushkala, 1999; van Haasteren et al., 1999)).

Searching genomic databases has revealed VRL-1, a subunit structurally related to VR1. Rat and human VRL-1 (AF129113 and AF129112, respectively) are ~49% identical and 66% similar to rat VR1 (AF029310)) (Caterina et al., 1999). Human VRL protein (AF103906) cloned by Wood and collegues (unpublished) is 99% identical to VRL-1 (AF129112). Recently, a patent application by Partiseti and Renard was published that described hVRCC (human vanilloid receptor like cation channel) which is nearly identical to AF129112 (the only difference is the deletion of Q418). We will refer to these sequences as VR2. Overall, the predicted structure of VR1 and VR2 is characteristic of a family of ion channels defined by the transient receptor potential (TRP) channels originally cloned from Drosophila melanogaster, a Ca-permeable channel that plays a role in phototransduction (Lu and Wong, 1987; Minke and Selinger, 1996). This receptor appears to also be involved in the sensation of pain-producing heat (Caterina et al., 1999). Expression of VR2 in oocytes and HEK cells usually conferred a sensitivity of the cells to noxious temperatures (>53 degC.), that was not sensitive to CPZ but was nearly completely blocked at 10 $\mu$M ruthenium red. Activation of VR2 induces a non-selective cation current with high permeability to Ca2+. Interestingly, the threshold for heat sensitivity decreased with repeated application of noxious stimuli, but not subthreshold temperatures (Caterina et al., 1999).

The rat SIC (stretch-inhibitable channel; Genbank AB015231), encoded by 529 amino acids, is thought to form an ion channel inhibited by stretch (Suzuki et al., 1999). The first 379 amino acids homologous to rat VR1. SIC lacks the large N-terminal cytoplasmic domain of the VR family but contains a sequence homologous to the A exon prior to the putative TM1. The last 163 amino acids, beginning in the middle of putative TM6 of rat SIC are similar to the corresponding amino acid sequence of the human VR3 A+B– of the present invention.

The present invention describes the cloning and function of a novel vanilloid receptor family member, VR3. This gene appears to be alternatively spliced to create at least 3 isoforms.

SUMMARY OF THE INVENTION

DNA molecules encoding 3 isoforms of the human vanilloid receptor 3 (hVR3) have been cloned and characterized. The biological and structural properties of these proteins are disclosed, as is the amino acid and nucleotide sequence. The recombinant protein is useful to identify modulators of the receptor VR3. Modulators identified in the assay disclosed herein are useful as therapeutic agents, which are candidates for the treatment of inflammatory conditions and for use as analgesics for intractable pain associated with postherpetic neuralgia, diabetic neuropathy, postmastectomy pain, complex regional pain syndromes, arthritis (e.g., rheumatoid and osteoarthritis), as well as ulcers, neurodegenerative diseases, asthma, chronic obstructive pulmonary disease, irritable bowel syndrome, and psoriasis. Uses include the treatment of central nervous system diseases, diseases of the intestinal tract, abnormal proliferation and cancer especially in the digestive system, prostate and female gonads, ulcer, liver disease, kidney disease, control of viscera innervated by the dorsal root ganglia, or to diagnose or treat any disorder related to abnormal expression of these hVR3 polypeptides, among others. In another aspect, the invention relates to methods to identify agonists and antagonists using the materials provided by the invention, and treating conditions associated with hVR3 imbalance. The recombinant DNA molecules, and portions thereof, are useful for isolating homologues of the DNA molecules, identifying and isolating genomic equivalents of the DNA molecules, and identifying, detecting or isolating mutant forms of the DNA molecules.

BRIEF DESCRIPTION OF THE DRAWING

FIGS. 1A and 1B—SEQ.ID.NO.:5. Human VR3A+B– nucleotide sequence of the coding region (2616 bp).

FIGS. 2A and 2B—SEQ.ID.NO.:6. The nucleotide sequence of human VR3A+B– is shown including 337 bp 5' untranslated region (UT) and 547 bp 3'UT (3500 bp).

FIG. 3—SEQ.ID.NO.:7. Coding sequence for human VR3A+B– (871 amino acids)

FIGS. 4A and 4B—SEQ.ID.NO.:8. Human VR3A–B– nucleotide sequence of the coding region (2436 bp).

FIG. 5—SEQ.ID.NO.:9. Coding sequence for human VR3A–B– (811 amino acids)

FIG. 6—SEQ.ID.NO.:10. Human VR3A+B+ nucleotide sequence of the coding region (2229 bp).

FIGS. 7A AND 7B—SEQ.ID.NO.:11. The nucleotide sequence of human VR3A+B+ is shown including 836 bp 5' UT and 994 bp 3'UT (4059 bp).

FIG. 8—SEQ.ID.NO.:12. Coding sequence for human VR3A+B+ (742 amino acids)

FIG. 9—Functional expression of VR3 isoforms in Xenopus oocytes is shown: viability of oocyte maintained in ND-96 with 2 $Ca^{2+}$was significantly diminished 4–6 days after injection with 3.25 ng VR3 A+B– and VR3 A+B+ (5 ng) but not VR3 A–B– (1.5 ng) cRNA. Data for VR3 A+B– and water-injected oocytes were obtained from 5 different experiments. Dead oocytes were determined visually. Data were analyzed using Chi square analysis.

FIG. 10A. Shown is the mean peak current elicited by a heat ramp from 25 deg C. to 46 deg C. and maintained at 46 degC. for at least 15 sec. The current is the increase over initial current at +80 mV. Voltage ramps were applied from –120 to +80 mV over 400 msec every 2 sec. Oocytes were injected with 3.25, 1.5 and 5 ng VR3 A+B–, A–B–, and A+B+ cRNA, respectively, and recorded up to 6 days later. Solid bar: water injected controls (n=8); clear bar: VR3 A+B– isoform (n=11); hatched bar: VR3 A–B– isoform (n=8); stippled bar: VR3 A+B+ isoform (n=5). All isoforms show a significant increase over water controls (p=0.001, 0.03 and 0.007, respectively; Student's t-test). The heat induced response is about 2-fold larger in the A+B– isoform compared to the other 2 isoforms but the differences are not significant (p=0.051 and p=0.16, for A+B– compared to A–B– and A+B+, respectively). Data were obtained from 2 sets of injected oocytes. Data shown is the mean and standard error of the mean. FIG. 10B. Voltage-ramp induced currents were recorded during application of increasing heat to oocytes injected with water (top), VR3 A+B– (second from top), VR3 A–B– ($3^{rd}$ from top), and VR3A+B+ (bottom). Oocytes were constantly perfused with Ca2+ ND-96 and the solution was heated by an inline heater device (TC-324B in conjunction with the SH-27A in line heater; Warner Instrument Corp.). Ramp induced currents (in uA, as indicated on the y-axis) obtained at temperatures from 37 deg C. to 46 deg C. are displayed; only current traces at the higher temperatures are labeled with the corresponding temperature.

FIG. 11A. An oocyte injected with VR1 cRNA [4 ng] was challenged with voltage ramps between –120 and +80 mV over 400 msec from a holding potential of –70 mV. The ramp-induced currents were increased after onset of perfusion of the oocyte at a rate of 10 ml/min. Preincubation with 10 uM ruthenium red for 0.5 min blocked the current. The block was partially reversible (not shown). FIG. 11B. An oocyte injected with VR1 cRNA [4 ng] together with VR3 A+B– [1.3 ng] was challenged with voltage ramps between –120 and +80 mV over 400 msec from a holding potential of –70 mV. The ramp-induced currents were increased after onset of perfusion of the oocyte at a rate of 10 ml/min. Preincubation with 10 uM ruthenium red for 0.5 min had little effect on $I_{perfusion}$. $I_{perfusion}$ had similar magnitudes in both sets of oocytes. Vrev for the RR inhibited current was about –13 mV (arrow).

FIG. 12A—VR3A+B– together with VR1. FIG. 12B—VR1 alone. The magnitude and decay kinetics of the response to 1 uM capsaicin was diminished when VR1 cRNA was co-expressed with VR3 A+B– cRNA at equal ratios [2.9 ng each].

FIG. 13—DNA array distribution analysis indicates that hVR3 mRNAs are expressed in a variety of tissues, and there is some overlap of expression with VR1 at a whole tissue level. The DNA sequence used on the DNA array is not present in A+B+, only A+B– and A–B– isoforms. Note that the cDNA species was cloned from pituitary and prostate glands.

DETAILED DESCRIPTION

Figure 10A:
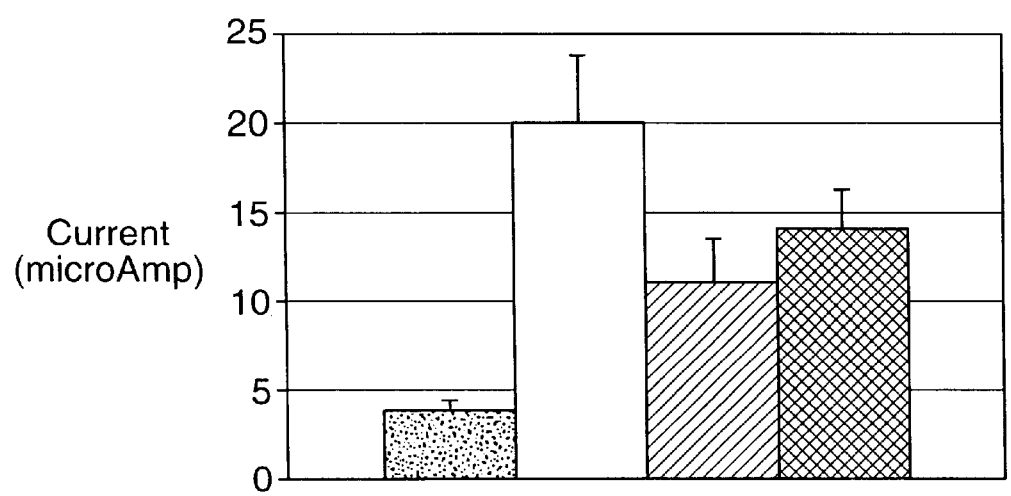
FIGS. 10A AND 10B—Function in oocytes: VR3 isoforms are activated by heat.

The present invention describes 3 isoforms of a human vanilloid receptor, termed VR3: VR3A+B–, VR3A–B–, and VR3A+B+. The nucleotide sequences of human VR3 receptor cDNAs revealed single large open reading frame of about 2616 (FIGS. 1A and 1B), 2436 (FIGS. 4A and 4B) and 2229 (FIG. 6) base pairs encoding 871 (FIG. 3), 811 (FIG. 5), and 742 (FIG. 8) amino acids for human VR3 A+B–, A–B– and A+B+, respectively. The cDNA for VR3 A+B– has 5' and 3'-untranslated extensions of about 337 and about 547 nucleotides, as shown in FIGS. 2A and 2B, wherein the 5'UTR is 1–337, the coding region is 338–2953, and the 3'UTR is 2954–3500. The cDNA for VR3 A+B+ has 5' and 3'-untranslated extensions of about 836 and about 994 nucleotides as shown in FIGS. 7A and 7B, wherein the 5'UTR is 1–836, the coding region is 837–3065, and the 3'UTR is 3066–4059. The first in-frame methionine was designated as the initiation codon for an open reading frame that predicts human VR3 receptor proteins with an estimated molecular mass ($M_r$) of about 98,242 Da, 91,294 Da and 83,310 Da for the isoforms A+B–, A–B– and A+B+, respectively. The A+B– isoform encodes a protein of 871 amino acids. The VR3 A–B– contains a deletion of 60 amino acids from amino acid 382 to 441 of VR3A+B–. VR3 A+B+ is identical to A+B– until amino acid 736 after which there are 6 divergent amino acids and a stop codon. The VR3 A+B+ isoform extends 20 amino acids after the putative TM6.

The predicted human VR3 receptor proteins were aligned with nucleotide and protein databases and are related to the vanilloid receptor family (VR1 and VR2). There are several conserved motifs found in this family of receptor including a large putative N-terminal hydrophilic segment (about 467 amino acids), three putative ankyrin repeat domains in the N-terminus region, 6 predicted transmembrane regions and a pore region. VR3 A+B– is 43% identical to human VR1, 39% identical to both human VRL-1 (AF129112) and human VRL (AF103906). Thus the VR3 receptor described herein is clearly a novel gene of the vanilloid receptor family.

Human VR3A+B– and VR3A–B– forms are similar to the rat stretch-inhibitable channel SIC [Genbank accession ABO15231] from amino acid 694 to the end. Rat SIC, encoded by 529 amino acids, is thought to form an ion channel inhibited by stretch. It lacks the large N-terminal cytoplasmic domain of the VR family but contains a sequence homologous to the A exon prior to the putative TM1.

The complete genomic sequence of the VR3 coding regions described herein appears to be found in a 380512 base pair sequence submission to Genbank (homo sapiens clone RPCI1-7G5 (AC007834), direct submission by Worley, K. C.). This Genbank entry list many fragments of DNA sequence and a proposed contiguous sequence, but lacks any analysis of the nucleic acid sequence and fails to characterize the features of the VR3 nucleic acid sequences, or describe the presence of the VR3 gene Isolation of Human VR3 Receptor Nucleic Acid The present invention relates to DNA encoding human VR3 receptor which were isolated from human VR3 receptor producing cells. Human VR3 receptor, as used herein, refers to protein which can specifically function as a human vanilloid receptor.

The complete amino acid sequence of human VR3 receptor was not previously known, nor was the complete nucleotide sequence encoding human VR3 receptor known. It is predicted that a wide variety of cells and cell types will contain the described human VR3 receptor.

Other cells and cell lines may also be suitable for use to isolate human VR3 receptor cDNA. Selection of suitable cells may be done by screening for human VR3 receptor activity in cell extracts or in whole cell assays, described herein. Cells that possess human VR3 receptor activity in any one of these assays may be suitable for the isolation of human VR3 receptor DNA or mRNA.

Any of a variety of procedures known in the art may be used to molecularly clone human VR3 receptor DNA. These methods include, but are not limited to, direct functional expression of the human VR3 receptor genes following the construction of a human VR3 receptor-containing cDNA library in an appropriate expression vector system. Another method is to screen human VR3 receptor-containing cDNA library constructed in a bacteriophage or plasmid shuttle vector with a labelled oligonucleotide probe designed from the amino acid sequence of the human VR3 receptor subunits. An additional method consists of screening a human VR3 receptor-containing cDNA library constructed in a bacteriophage or plasmid shuttle vector with a partial cDNA encoding the human VR3 receptor protein. This partial cDNA is obtained by the specific PCR amplification of human VR3 receptor DNA fragments through the design of degenerate oligonucleotide primers from the amino acid sequence of the purified human VR3 receptor protein.

Another method is to isolate RNA from human VR3 receptor-producing cells and translate the RNA into protein via an in vitro or an in vivo translation system. The translation of the RNA into a peptide a protein will result in the production of at least a portion of the human VR3 receptor protein which can be identified by, for example, immunological reactivity with an anti-human VR3 receptor antibody or by biological activity of human VR3 receptor protein. In this method, pools of RNA isolated from human VR3 receptor-producing cells can be analyzed for the presence of an RNA that encodes at least a portion of the human VR3 receptor protein. Further fractionation of the RNA pool can be done to purify the human VR3 receptor RNA from non-human VR3 receptor RNA. The peptide or protein produced by this method may be analyzed to provide amino acid sequences which in turn are used to provide primers for production of human VR3 receptor cDNA, or the RNA used for translation can be analyzed to provide nucleotide sequences encoding human VR3 receptor and produce probes for this production of human VR3 receptor cDNA. This method is known in the art and can be found in, for example, Maniatis, T., Fritsch, E. F., Sambrook, J. in *Molecular Cloning: A Laboratory Manual*, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating human VR3 receptor-encoding DNA. Other types of libraries include, but are not limited to, cDNA libraries derived from other cells, from organisms other than human VR3 receptor, and genomic DNA libraries that include YAC (yeast artificial chromosome) and cosmid libraries.

It is readily apparent to those skilled in the art that suitable cDNA libraries may be prepared from cells or cell lines which have human VR3 receptor activity. The selection of cells or cell lines for use in preparing a cDNA library to isolate human VR3 receptor cDNA may be done by first measuring cell associated human VR3 receptor activity using the measurement of human VR3 receptor-associated biological activity or a ligand binding assay.

Preparation of CDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding human VR3 receptor may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the human VR3 receptor gene by the above methods, the amino acid sequence of human VR3 receptor may be necessary. To accomplish this, human VR3 receptor protein may be purified and partial amino acid sequence determined by automated sequenators. It is not necessary to determine the entire amino acid sequence, but the linear sequence of two regions of 6 to 8 amino acids from the protein is determined for the production of primers for PCR amplification of a partial human VR3 receptor DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human VR3 receptor sequence but will be capable of hybridizing to human VR3 receptor DNA even in the presence of DNA oligonucleotides with mismatches. The mismatched DNA oligonucleotides may still sufficiently hybridize to the human VR3 receptor DNA to permit identification and isolation of human VR3 receptor encoding DNA. DNA isolated by these methods can be used to screen DNA libraries from a variety of cell types, from invertebrate and vertebrate sources, and to isolate homologous genes.

Purified biologically active human VR3 receptor may have several different physical forms. human VR3 receptor may exist as a full-length nascent or unprocessed polypeptide, or as partially processed polypeptides or combinations of processed polypeptides. The full-length nascent human VR3 receptor polypeptide may be posttranslationally modified by specific proteolytic cleavage events that results in the formation of fragments of the full length nascent polypeptide. A fragment, or physical association of fragments may have the full biological activity associated with human VR3 receptor however, the degree of human VR3 receptor activity may vary between individual human VR3 receptor fragments and physically associated human VR3 receptor polypeptide fragments.

Because the genetic code is degenerate, more than one codon may be used to encode a particular amino acid, and therefore, the amino acid sequence can be encoded by any of a set of similar DNA oligonucleotides. Only one member of the set will be identical to the human VR3 receptor sequence but will be capable of hybridizing to human VR3 receptor DNA even in the presence of DNA oligonucleotides with mismatches under appropriate conditions. Under alternate conditions, the mismatched DNA oligonucleotides may still hybridize to the human VR3 receptor DNA to permit identification and isolation of human VR3 receptor encoding DNA.

DNA encoding human VR3 receptor from a particular organism may be used to isolate and purify homologues of human VR3 receptor from other organisms. To accomplish this, the first human VR3 receptor DNA may be mixed with a sample containing DNA encoding homologues of human VR3 receptor under appropriate hybridization conditions. The hybridized DNA complex may be isolated and the DNA encoding the homologous DNA may be purified therefrom.

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein that do not substantially alter the ultimate physical properties of the expressed protein. For example, substitution of valine for leucine, arginine for lysine, or asparagine for glutamine may not cause a change in functionality of the polypeptide. Such substitutions are well known and are described, for instance in *Molecular Biology of the Gene*, 4$^{th}$ Ed. Benjamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residues that may result in a silent mutation, a conservative mutation, or a nonconservative mutation. Chimeric genes are prepared by swapping domains of similar or different genes to replace similar domains in the human VR3 receptor gene. Similarly, fusion genes may be prepared that add domains to the human VR3 receptor gene, such as an affinity tag to facilitate identification and isolation of the gene. Fusion genes may be prepared to replace regions of the human VR3 receptor gene, for example to create a soluble version of the protein by removing a transmembrane domain or adding a targeting sequence to redirect the normal transport of the protein, or adding new post-translational modification sequences to the human VR3 receptor gene. Examples of altered properties include but are not limited to changes in the affinity of an enzyme for a substrate or a receptor for a ligand.

As used herein, a "functional derivative" of human VR3 receptor is a compound that possesses a biological activity (either functional or structural) that is substantially similar to the biological activity of human VR3 receptor. The term "functional derivatives" is intended to include the "fragments," "variants," "degenerate variants," "analogs" and "homologues" or to "chemical derivatives" of human VR3 receptor. The term "fragment" is meant to refer to any polypeptide subset of human VR3 receptor. The term "variant" is meant to refer to a molecule substantially similar in structure and function to either the entire human VR3 receptor molecule or to a fragment thereof. A molecule is "substantially similar" to human VR3 receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire human VR3 receptor molecule or to a fragment thereof.

Recombinant Expression of Human VR3 Receptor

The cloned human VR3 receptor DNA obtained through the methods described herein may be recombinantly expressed by molecular cloning into an expression vector containing a suitable promoter and other appropriate transcription regulatory elements, and transferred into prokaryotic or eukaryotic host cells to produce recombinant human VR3 receptor protein. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant Human VR3 receptor in mammalian cells. Commercially available mammalian expression vectors which may be suitable for recombinant Human VR3 receptor expression, include but are not limited to, pMAM-neo (Clontech), pcDNA3 (InVitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant human VR3 receptor in bacterial cells. Commercially available bacterial expression vectors which may be suitable for recombinant human VR3 receptor expression include, but are not limited to pET vectors (Novagen) and pQE vectors (Qiagen).

A variety of fungal cell expression vectors may be used to express recombinant human VR3 receptor in fungal cells such as yeast. Commercially available fungal cell expression vectors which may be suitable for recombinant human VR3 receptor expression include but are not limited to pYES2 (InVitrogen) and Pichia expression vector (InVitrogen). A variety of insect cell expression vectors may be used to express recombinant human VR3 receptor in insect cells. Commercially available insect cell expression vectors which may be suitable for recombinant expression of human VR3 receptor include but are not limited to pBlueBacII (InVitrogen).

DNA encoding human VR3 receptor may be cloned into an expression vector for expression in a recombinant host cell. Recombinant host cells may be prokaryotic or eukaryotic, including but not limited to bacteria such as E. coli fungal cells such as yeast, mammalian cells including but not limited to cell lines of human, bovine, porcine, monkey and rodent origin, and insect cells including but not limited to drosophila and silkworm derived cell line. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce human VR3 receptor protein. Identification of human VR3 receptor expressing host cell clones may be done by several means, including but not limited to immunological reactivity with anti-human VR3 receptor antibodies, and the presence of host cell-associated human VR3 receptor activity.

Expression of human VR3 receptor DNA may also be performed using in vitro produced synthetic mRNA. Synthetic mRNA or mRNA isolated from Human VR3 receptor producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the human VR3 receptor DNA sequence(s) that yields optimal levels of human VR3 receptor activity and/or human VR3 receptor protein, human VR3 receptor DNA molecules including, but not limited to, the following can be constructed:

| Gene name | Start codon | End codon | total base pairs |
| --- | --- | --- | --- |
| VR3A+B+ | 837 | 3065 | 2229 |
| VR3A+B− | 338 | 2953 | 2616 |
| VR3A−B− | 1 | 2436 | 2436 |

(these numbers correspond to first nucleotide of first methionine and last nucleotide before the first stop codon) and several constructs containing portions of the CDNA encoding human VR3 receptor protein. All constructs can be designed to contain none, all or portions of the 5' or the 3' untranslated region of human VR3 receptor cDNA. Human VR3 receptor activity and levels of protein expression can be determined following the introduction, both singly and in combination, of these constructs into appropriate host cells. Following determination of the human VR3 receptor DNA cassette yielding optimal expression in transient assays, this Human VR3 receptor DNA construct is transferred to a variety of expression vectors, for expression in host cells including, but not limited to, mammalian cells, baculovirus-infected insect cells, E. coli, and the yeast S. cerevisiae.

Assay Methods for Human VR3 Receptor

Host cell transfectants and microinjected oocytes may be used to assay both the levels of functional Human VR3 receptor activity and levels of total human VR3 receptor protein by the following methods. In the case of recombinant host cells, this involves the co-transfection of one or possibly two or more plasmids, containing the human VR3 receptor DNA encoding one or more fragments, subunits, or other functional gene. In the case of oocytes, this involves the co-injection of synthetic RNAs for human VR3 receptor protein. Following an appropriate period of time to allow for expression, cellular protein is metabolically labelled with, for example $^{35}$S-methionine for 24 hours, after which cell lysates and cell culture supernatants are harvested and subjected to immunoprecipitation with polyclonal antibodies directed against the human VR3 receptor protein.

Levels of human VR3 receptor protein in host cells are quantitated by immunoaffinity and/or ligand affinity techniques. Human VR3 receptor-specific affinity beads or human VR3 receptor-specific antibodies are used to isolate for example $^{35}$S-methionine labelled or unlabelled human VR3 receptor protein. Labelled human VR3 receptor protein is analyzed by SDS-PAGE. Unlabelled human VR3 receptor protein is detected by Western blotting, ELISA or RIA assays employing human VR3 receptor specific antibodies.

Other methods for detecting human VR3 receptor activity involve the direct measurement of human VR3 receptor activity in whole cells transfected with human VR3 receptor cDNA or oocytes injected with human VR3 receptor mRNA. Human VR3 receptor activity is measured by specific ligand binding or biological characteristics of the host cells expressing human VR3 receptor DNA. In the case of recombinant host cells expressing human VR3 receptor patch voltage clamp techniques can be used to measure channel activity and quantitate human VR3 receptor protein. In the case of oocytes patch clamp as well as two-electrode voltage clamp techniques can be used to measure calcium channel activity and quantitate human VR3 receptor protein.

Cell Based Assays

The present invention provides a whole cell method to detect compound modulation of human VR3 receptor. The method comprises the steps;

1) contacting a compound, and a cell that contains functional human VR3 receptor, and
2) measuring a change in the cell in response to modified human VR3 receptor function by the compound.

The amount of time necessary for cellular contact with the compound is empirically determined, for example, by running a time course with a known human VR3 receptor modulator and measuring cellular changes as a function of time.

The measurement means of the method of the present invention can be further defined by comparing a cell that has been exposed to a compound to an identical cell that has not been similarly expose to the compound. Alternatively two cells, one containing functional human VR3 receptor and a second cell identical to the first, but lacking functional human VR3 receptor could be both be contacted with the same compound and compared for differences between the two cells. This technique is also useful in establishing the background noise of these assays. One of average skill in the art will appreciate that these control mechanisms also allow easy selection of cellular changes that are responsive to modulation of functional human VR3 receptor.

The term "cell" refers to at least one cell, but includes a plurality of cells appropriate for the sensitivity of the detection method. Cells suitable for the present invention may be bacterial, yeast, or eukaryotic.

The assay methods to determine compound modulation of functional human VR3 receptor can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include but are not limited to, 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The cellular changes suitable for the method of the present invention comprise directly measuring changes in the activity, function or quantity of human VR3 receptor, or by measuring downstream effects of human VR3 receptor function, for example by measuring secondary messenger concentrations or changes in transcription or by changes in protein levels of genes that are transcriptionally influenced by human VR3 receptor, or by measuring phenotypic changes in the cell. Preferred measurement means include changes in the quantity of human VR3 receptor protein, changes in the functional activity of human VR3 receptor, changes in the quantity of mRNA, changes in intracellular protein, changes in cell surface protein, or secreted protein, or changes in Ca+2, cAMP or GTP concentration. Changes in the quantity or functional activity of human VR3 receptor are described herein. Changes in the levels of mRNA are detected by reverse transcription polymerase chain reaction (RT-PCR) or by differential gene expression. Immunoaffinity, ligand affinity, or enzymatic measurement quantitates VR3 induced changes in levels of specific proteins in host cells. Where the protein is an enzyme, the induction of protein is monitored by cleavage of a flourogenic or colorimetric substrate.

Preferred detection means for cell surface protein include flow cytometry or statistical cell imaging. In both techniques the protein of interest is localized at the cell surface, labeled with a specific fluorescent probe, and detected via the degree of cellular fluorescence. In flow cytometry, the cells are analyzed in a solution, whereas in cellular imaging techniques, a field of cells is compared for relative fluorescence.

The present invention is also directed to methods for screening for compounds that modulate the expression of DNA or RNA encoding human VR3 receptor as well as the function of human VR3 receptor protein in vivo. Compounds may modulate by increasing or attenuating the expression of DNA or RNA encoding human VR3 receptor, or the function of human VR3 receptor protein. Compounds that modulate the expression of DNA or RNA encoding human VR3 receptor or the function of human VR3 receptor protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, and human VR3 receptor.

Purification of Human VR3 Receptor Protein

Following expression of human VR3 receptor in a recombinant host cell, human VR3 receptor protein may be recovered to provide purified human VR3 receptor. Recombinant human VR3 receptor may be purified from cell lysates and extracts, by various combinations of, or individual application of salt fractionation, ion exchange chromatography, size exclusion chromatography, hydroxylapatite adsorption chromatography and hydrophobic interaction chromatography, lectin chromatography, and antibody/ligand affinity chromatography.

Recombinant human VR3 receptor can be separated from other cellular proteins by use of an immunoaffinity column made with monoclonal or polyclonal antibodies specific for full length nascent human VR3 receptor, polypeptide fragments of human VR3 receptor or human VR3 receptor subunits. The affinity resin is then equilibrated in a suitable buffer, for example phosphate buffered saline (pH 7.3), and the cell culture supernatants or cell extracts containing human VR3 receptor or human VR3 receptor subunits are slowly passed through the column. The column is then washed with the buffer until the optical density ($A_{280}$) falls to background, then the protein is eluted by changing the buffer condition, such as by lowering the pH using a buffer such as 0.23 M glycine-HC1 (pH 2.6). The purified Human VR3 receptor protein is then dialyzed against a suitable buffer such as phosphate buffered saline.

Production and Use of Antibodies that Bind to Human VR3 Receptor

Monospecific antibodies to human VR3 receptor are purified from mammalian antisera containing antibodies reactive against human VR3 receptor or are prepared as monoclonal antibodies reactive with human VR3 receptor using the technique originally described by Kohler and Milstein, *Nature* 256: 495–497 (1975). Immunological techniques are well known in the art and described in, for example, *Antibodies: A laboratory manual* published by Cold Spring Harbor Laboratory Press, Cold Spring Harbor, N.Y., ISBN 0879693142. Monospecific antibody as used herein is defined as a single antibody species or multiple antibody species with homogenous binding characteristics for human VR3 receptor. Homogenous binding as used herein refers to the ability of the antibody species to bind to a specific antigen or epitope, such as those associated with the human VR3 receptor, as described above. Human VR3 receptor specific antibodies are raised by immunizing animals such as mice, rats, guinea pigs, rabbits, goats, horses and the like, with rabbits being preferred, with an appropriate concentration of human VR3 receptor either with or without an immune adjuvant.

Preimmune serum is collected prior to the first immunization. Each animal receives between about 0.001 mg and about 100 mg of human VR3 receptor associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human VR3 receptor in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with human VR3 receptor are prepared by immunizing inbred mice, preferably Balb/c, with human VR3 receptor. The mice are immunized by the IP or SC route with about 0.001 mg to about 1.0 mg, preferably about 0.1 mg, of human VR3 receptor in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 to about 1.0 mg of human VR3 receptor in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using human VR3 receptor as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Knuse and Paterson, Eds., Academic Press, 1973 or by the technique of limited dilution.

Monoclonal antibodies are produced in vivo by injection of pristane primed Balb/c mice, approximately 0.5 ml per mouse, with about $1\times10^6$ to about $6\times10^6$ hybridoma cells at least about 4 days after priming. Ascites fluid is collected at approximately 8–12 days after cell transfer and the monoclonal antibodies are purified by techniques known in the art.

In vitro production of anti-human VR3 receptor mAb is carried out by growing the hybridoma in tissue culture media well known in the art. High density in vitro cell culture may be conducted to produce large quantities of anti-human VR3 receptor MAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human VR3 receptor in body fluids or tissue and cell extracts.

It is readily apparent to those skilled in the art that the above described methods for producing monospecific antibodies may be utilized to produce antibodies specific for human VR3 receptor polypeptide fragments, or full-length nascent human VR3 receptor polypeptide, or the individual human VR3 receptor subunits. Specifically, it is readily apparent to those skilled in the art that monospecific antibodies may be generated which are specific for only one human VR3 receptor subunit or the fully functional human VR3 receptor protein. It is also apparent to those skilled in the art that monospecific antibodies may be generated that inhibit normal function of human VR3 receptor protein.

Human VR3 receptor antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfhydryl groups on antibodies are well known in the art; amine groups are reactive with, for example, N-hydroxysuccinimide esters.

Kit Compositions Containing Human VR3 Receptor Specific Reagents

Kits containing human VR3 receptor DNA or RNA, antibodies to human VR3 receptor, or human VR3 receptor protein may be prepared. Such kits are used to detect DNA that hybridizes to human VR3 receptor DNA or to detect the presence of human VR3 receptor protein or peptide fragments in a sample. Such characterization is useful for a variety of purposes including but not limited to forensic analyses, diagnostic applications, and epidemiological studies.

This invention relates to the use of human VR3 polynucleotides for the use as diagnostic reagents. Detection of a mutated form of human VR3 gene associated with a dysfunction will provide a diagnostic tool that can add to or define a diagnosis of a disease or susceptibility to a disease which results from under-expression or over-expression of human VR3. Individuals carrying mutations in the human VR3 gene may be detected at the DNA level by a variety of techniques well known in the are, and described herein.

The DNA molecules, RNA molecules, recombinant protein and antibodies of the present invention may be used to screen and measure levels of human VR3 receptor DNA, human VR3 receptor RNA or human VR3 receptor protein. The recombinant proteins, DNA molecules, RNA molecules and antibodies lend themselves to the formulation of kits suitable for the detection and typing of human VR3 receptor. Such a kit would comprise a compartmentalized carrier suitable to hold in close confinement at least one container. The carrier would further comprise reagents such as recombinant human VR3 receptor protein or anti-human VR3 receptor antibodies suitable for detecting human VR3 receptor. The carrier may also contain a means for detection such as labeled antigen or enzyme substrates or the like.

Gene Therapy

Nucleotide sequences that are complementary to the human VR3 receptor encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other Human VR3 receptor antisense oligonucleotide mimetics. Human VR3 receptor antisense molecules may be introduced into cells by microinjection, liposome encapsulation or by expression from vectors harboring the antisense sequence. Human VR3 receptor antisense therapy may be particularly useful for the treatment of diseases where it is beneficial to reduce human VR3 receptor activity.

Human VR3 receptor gene therapy may be used to introduce human VR3 receptor into the cells of target organisms. The human VR3 receptor gene can be ligated into viral vectors that mediate transfer of the human VR3 receptor DNA by infection of recipient host cells. Suitable viral vectors include retrovirus, adenovirus, adeno-associated virus, herpes virus, vaccinia virus, poliovirus and the like. Alternatively, human VR3 receptor DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo human VR3 receptor gene therapy. Human VR3 receptor gene therapy may be particularly useful for the treatment of diseases where it is beneficial to elevate human VR3 receptor activity. Protocols for molecular methodology of gene therapy suitable for use with the human VR3 receptor gene is described in *Gene Therapy Protocols*, edited by Paul D. Robbins, Human press, Totawa N.J., 1996.

Pharmaceutical Compositions

Pharmaceutically useful compositions comprising human VR3 receptor DNA, human VR3 receptor RNA, or human VR3 receptor protein, or modulators of human VR3 receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of Human VR3 receptor-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the human VR3 receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of human VR3 receptor can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a human VR3 receptor-modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the human VR3 receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Generation of Human Prostate and Pituitary cDNA Libraries cDNA Synthesis

First Strand Synthesis

Approximately 5 µg of human prostate or pituitary mRNA (Clontech) was used to synthesize cDNA using the cDNA synthesis kit (Life Technologies). Two microliters of Not1 primer adapter was added to 5 µl of mRNA and the mixture was heated to 70° C. for 10 minutes and placed on ice. The following reagents were added on ice: 41 µl of 5×first strand buffer (250 mM TRIS-HCl (pH8.3), 375mM KCl, 15 mM MgCl$_2$), 2 μl of 0.1M DTT, 10 mM dNTP (nucleotide triphosphates) mix and 1 μl of DEPC treated water. The reaction was incubated at 42° C. for 5 minutes. Finally, 5 μl of Superscript RT II was added and incubated at 42° C. for 2 more hours. The reaction was terminated on ice.

Second Strand Synthesis

The first strand product was adjusted to 93 μl with water and the following reagents were added on ice: 30 μl of 5×2nd strand buffer (100 mM TRIS-HCl (pH6.9), 450 mM KCl, 23 mM MgCl$_2$, 0.75 mM β-NAD+, 50 mM (NH$_4$)$_2$SO$_4$), 3 μl of 10 mM dNTP (nucleotide triphosphates), 1 μl E. coli DNA ligase (10 units) 1 μl RNase H (2 units), 4 μl DNA pol I (10 units). The reaction was incubated at 16° C. for 2 hours. The DNA from second strand synthesis was treated with T4 DNA polymerase and placed at 16° C. to blunt the DNA ends. The double stranded cDNA was extracted with 150 μl of a mixture of phenol and chloroform (1:1, v:v) and precipitated with 0.5 volumes of 7.5 M NH4OAc and 2 volumes of absolute ethanol. The pellet was washed with 70% ethanol and dried down at 37° C. to remove the residual ethanol. The double stranded DNA pellet was resuspended in 25 μl of water and the following reagents were added; 10 μl of 5×T4 DNA ligase buffer, 10 μl of Sal1 adapters and 5 μl of T4 DNA ligase. The ingredients were mixed gently and ligated overnight at 16° C. The ligation mix was extracted with phenol:chloroform:isoamyl alcohol, vortexed thoroughly and centrifuged at room temperature for 5 minutes at 14,000×g to separate the phases. The aqueous phase was transferred to a new tube and the volume adjusted to 100 ml with water. The purified DNA was size selected on a chromaspin 1000 column (Clontech) to eliminate the smaller cDNA molecules. The double stranded DNA was digested with Not1 restriction enzyme for 3–4 hours at 37° C. The restriction digest was electrophoresed on a 0.8% low melt agarose gel. The cDNA in the range of 1–5 kb was cut out and purified using Gelzyme (InVitrogen). The product was extracted with phenol:chloroform and precipitated with NH$_4$OAc and absolute ethanol. The pellet was washed with 70% ethanol and resuspended in 10 ml of water.

Ligation of cDNA to the Vector

The cDNA was split up into 5 tubes (2μl each) and the ligation reactions were set up by adding 4.5 μl of water, 2 pl of 5× ligation buffer, 1 μl of p-Sport vector DNA (cut with Sal-1/Not1 and phosphatase treated) and 0.5 μl of T4 DNA ligase. The ligation was incubated at 40° C. overnight.

Introduction of Ligated cDNA into E. coli by Electroporation

The ligation reaction volume was adjusted to a total volume of 20 μl with water. Five milliliters of yeast tRNA, 12.5 ml of 7.5M NH$_4$OAc and 70 ml of absolute ethanol (−20° C.) was added. The mixture was vortexed thoroughly, and immediately centrifuged at room temperature for 20 minutes at 14000×g. The pellets were washed in 70% ethanol and each pellet was resuspended in 5 ml of water. All 5 ligations (25 ml) were pooled and 100μl of DH10B electro-competent cells (Life Technologies) were electroporated with 1 ml of DNA (total of 20 electroporations), then plated out on ampicillin plates to determine the number of recombinants (cfu) per microliter. The entire library was seeded into 2 liters of Super Broth and maxipreps were made using Promega Maxi Prep kit and purified on cesium chloride gradients.

EXAMPLE 2

Library Screening/Human VR3 A+B+ Generation
Human Pituitary Gland Library Screening One-microliter aliquots of the human pituitary gland-library were electroporated into Electromax DH10B cells (Life Technologies). The volume was adjusted to 1 ml with SOC media and incubated for 45 minutes at 37° C. with shaking. The library was then plated out on 150 cm$^2$plates containing LB to a density of 20000 colonies per plate. These cultures were grown overnight at 37° C.

A human VR3 receptor probe was generated by polymerase chain reaction using the following primer pair:

5' oligo (SEQ.ID. NO.:1): 5' ACCGGCCTATCCTCTTTGA-CATCGTG

3' oligo (SEQ.ID.NO.:2): 5' TGTCCGCCTTCTTGTGGGGGT-TCTC

The probe was generated by PCR using regular PCR conditions using 5' and 3' probe oligos (100 ng each) and 10 ng of diluted miniprep DNA. The resulting 493 bp fragment was run on 1% agarose gel and purified using a QUIAquick Gel extraction kit (Quiagen). About 100 ng of the purified probe was labeled with alpha 32P using oligolabeling kit from Pharmacia and the labeled DNA was purified with S-200 columns (Pharmacia).

The library colonies were lifted on Protran nitrocellulose filters (Scheicher & Schuel) and the DNA was denatured in 1.5 M NaCl, 0.5 M NaOH. The filter disks were neutralized with 1.5 M NaCl, 1.0 M Tris-HCl, pH 7.5 and then UV crosslinked to the membrane using a UV-Stratalinker (Stratagene). The filters were washed several times in wash solution (1 M Tris-HCl, pH 8.0; 5 M NaCl; 0.5 M EDTA; 20% SDS) at 42° C. Then the disks were incubated in 1× southern pre-hybridization buffer (5'-3' Inc) containing 50% formamide and 100 ug/ml of sheared salmon sperm DNA (5'-3' Inc) for 6 hours at 42 C. Finally, hybridization was performed overnight at 42 C. in 1× hybridization buffer (5'-3') containing 50% formamide, 100 ng of sheared salmon sperm DNA in the presence of labeled probe (5×10$^5$ to 1×10$^6$ cmp/ml of hybridization buffer).

The disks were washed twice in 2×SSC, 0.2% SDS at room temperature (20 minutes each) and once in 0.2×SSC, 0.1%SDS at 50 C. for 30 minutes. The membranes were than placed on sheets of filter paper, wrapped in the plastic wrap and exposed to the film at −20 C. overnight.

Positive clones were identified and collected by coring the colonies from the original plate. The colonies were incubated in LB for 1 hour at 37° C. Dilutions of the cultures were plated onto LB agar plates and the filter-lifting, hybridizing, washing, colony-picking procedure was repeated. Individual clones from the second screen were picked and digested with SalI/NotI to determine the size of the inserts, and the inserts were sequenced.

The full length clone was generated by PCR with Pfu polymerase using 10 ng of the sequenced library clone as a template and full length oligos with KpnI (FL 5' oligo SEQ.ID.NO.3) and NotI (FL 3' oligo SEQ.ID.NO.4) sites.

FL 5' oligo (SEQ.ID.NO.3): AACGTTGGTACCGCCACCATG-GCGGATTCCAGCGAAGGCCCCCGCGCG

FL3' oligo: (SEQ.ID.NO.4): TAAAGCGGCCGCTTCAGGAGG-GACATCGGTGAGCCTCAC

The PCR product was digested with KpnI and NotI enzymes and cloned into a pSP64T.GC expression vector. Large-scale preparation of DNA was done using a MEGA prep kit (Quiagen).

EXAMPLE 3

Library Screening/Human VR3 A+B− and Human VR3 A−B− Generation

Human Prostate Library Screening

One microliter aliquots of the human prostate library were electroporated into Electromax DH10B cells (Life Technologies). The volume was adjusted to 1 ml with SOC media and incubated for 45 minutes at 37° C. with shaking. The library was then plated out on 150 cm² plates containing LB to a density of 20000 colonies per plate. These cultures were grown overnight at 37° C.

A human VR3 receptor probe was generated by polymerase chain reaction using the following primer pair:

5' oligo (SEQ.ID. NO.:13): 5' CTACCTGACGGAGAACCCCCA-CAAG

3' oligo (SEQ.ID.NO.:14): 5' GTAGTAGGCGGTGAGACTGAA-GATGA

The probe was generated by PCR using regular PCR conditions using 5' and 3' probe oligos (100 ng each) and 10 ng of diluted miniprep DNA. The resulting 387 bp fragment was run on 1% agarose gel and purified using a QUIAquick Gel extraction kit (Quiagen). About 100 ng of the purified probe was labeled with alpha 32P using oligolabeling kit from Pharmacia and the labeled DNA was purified with S-200 columns (Pharmacia).

The library colonies were lifted on Protran nitrocellulose filters (Schleicher & Schuel) and the DNA was denatured in 1.5 M NaCl, 0.5 M NaOH. The filter disks were neutralized with 1.5 M NaCl, 1.0 M Tris-HCl, pH 7.5 and then UV crosslinked to the membrane using a UV-Stratalinker (Stratagene). The filters were washed several times in wash solution (1 M Tris-HCl, pH 8.0; 5 M NaCl; 0.5 M EDTA; 20% SDS) at 42° C. Then the disks were incubated in 1× southern pre-hybridization buffer (5'-3' Inc) containing 50% formamide and 100 ug/ml of sheared salmon sperm DNA (5'-3' Inc) for 6 hours at 42 C. Finally, hybridization was performed overnight at 42 C. in 1× hybridization buffer (5'-3') containing 50% formamide, 100 ng of sheared salmon sperm DNA in the presence of labeled probe (5×10⁵ to 1×10⁶ cmp/ml of hybridization buffer).

The disks were washed twice in 2×SSC, 0.2% SDS at room temperature (20 minutes each) and once in 0.2×SSC, 0.1%SDS at 50 C. for 30 minutes. The membranes were than placed on sheets of filter paper, wrapped in the Saran wrap and exposed to the film at −20 C. overnight.

Positive clones were identified and collected by coring the colonies from the original plate. The colonies were incubated in LB for 1 hour at 37° C. Dilutions of the cultures were plated onto LB agar plates and the filter-lifting, hybridizing, washing, colony-picking procedure was repeated. Individual clones from the second screen were picked and digested with EcoRI/NotI to determine the size of the inserts, and the inserts were sequenced.

The full length clone was generated by PCR with Pfu polymerase using 10 ng of the sequenced library clone as a template and full length oligos with NotI (FL 5'oligo SEQ.ID.NO.:15) and XbaI (FL 3' oligo SEQ.ID.NO.:16) sites.

FL 5' oligo (SEQ.ID.NO.:15): 5'AACGTTGGCGGCCGCGCCAC-CATGGCGGATTCCAGCGAAGGCCCCCGCG CG FL3' oligo: (SEQ.ID.NO.:16): 5' AACGTTTCTAGACTGGGCTG-CAGTCCCTAG The PCR product was digested with NotI and XbaI enzymes and cloned into a pgem HE expression vector. Large-scale preparation of DNA was done using a MEGA prep kit (Quiagen).

EXAMPLE 4

Cloning Human VR3 Receptor cDNA into a Mammalian Expression Vector

The human VR3 receptor cDNAs (collectively referred to as hVR3) were cloned into the mammalian expression vector pcDNA3.1/Zeo(+). The cloned PCR product was purified on a column (Wizard PCR DNA purification kit from Promega) and digested with Not I and EcoRI (NEB) to create cohesive ends. The product was purified by electrophoresis on a low melting point agarose gel. The pcDNA3.1/Zeo(+) vector was digested with Not1 and XbaI (except for hVR3 A+B+, which was cloned into BamHI/NotI sites) enzymes and subsequently purified on a low melting point agarose gel. The linear vector was used to ligate to the human VR3 cDNA inserts. Recombinants were isolated, designated human VR3 receptor, and used to transfect mammalian cells (HEK293, COS-7 or CHO-K1 cells) using the Effectene non-liposomal lipid based transfection kit (Quiagen). Stable cell clones were selected by growth in the presence of zeocin. Single zeocin resistant clones were isolated and shown to contain the intact human VR3 receptor gene. Clones containing the human VR3 receptor cDNAs were analyzed for hVR3 protein expression. Recombinant plasmids containing human VR3 encoding DNA were used to transform the mammalian COS or CHO cells or HEK293 cells.

Cells expressing human VR3 receptor, stably or transiently, are used to test for expression of human VR3 receptor and for ³H-RTX binding activity. These cells are used to identify and examine other compounds for their ability to modulate, inhibit or activate the human VR3 receptor and to compete for radioactive ³H-RTX binding.

Cassettes containing the human VR3 receptor cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants are harvested and analyzed for human VR3 receptor expression as described herein.

All of the vectors used for mammalian transient expression can be used to establish stable cell lines expressing human VR3 receptor. Unaltered humanVR3 receptor cDNA constructs cloned into expression vectors are expected to program host cells to make human VR3 receptor protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing human VR3 receptor cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of human VR3 receptor are quantitated by the assays described herein.

Human VR3 receptor cDNA constructs are also ligated into vectors containing amplifiable drug-resistance markers for the production of mammalian cell clones synthesizing the highest possible levels of human VR3 receptor. Following introduction of these constructs into cells, clones containing the plasmid are selected with the appropriate agent, and isolation of an over-expressing clone with a high copy number of plasmids is accomplished by selection in increasing doses of the agent.

The expression of recombinant human VR3 receptor is achieved by transfection of full-length human VR3 receptor cDNA into a mammalian host cell.

EXAMPLE 5

Characterization of Functional Protein Encoded by pVR3R in *Xenopus* oocytes

*Xenopus laevis* oocytes were prepared and injected using standard methods previously described and known in the art (Fraser et al., 1993). Ovarian lobes from adult female *Xenopus laevis* (Nasco, Fort Atkinson, Wis.) were teased apart, rinsed several times in nominally Ca-free saline containing: 82.5 mM NaCl, 2.5 mM KCl, 1 mM $MgCl_2$, 5 mM HEPES, adjusted to pH 7.0 with NaOH (OR-2), and gently shaken in OR-2 containing 0.2% collagenase Type 1 (ICN Biomedicals, Aurora, Ohio) for 2–5 hours. When approximately 50% of the follicular layers were removed, Stage V and VI oocytes were selected and rinsed in media consisting of 75% OR-2 and 25% ND-96. The ND-96 contained: 100 mM NaCl, 2 mM KCl, 1 mM $MgCl_2$, 1.8 mM $CaCl_2$, 5 mM HEPES, 2.5 mM Na pyruvate, gentamicin (50 ug/ml), adjusted to pH 7.0 with NaOH. The extracellular $Ca^{+2}$ was gradually increased and the cells were maintained in ND-96 for 2–24 hours before injection. For in vitro transcription, pGEM HE (Liman et al., 1992) containing human VR3 was linearized with NheI and transcribed with T7 RNA polymerase (Promega) in the presence of the cap analog m7G(5')ppp(5')G. The synthesized cRNA was precipitated with ammonium acetate and isopropanol, and resuspended in 50 µl nuclease-free water. cRNA was quantified using formaldehyde gels (1% agarose, 1×MOPS, 3% formaldehyde) against 1,2 and 5 µl RNA markers (Gibco BRL, 0.24–9.5 Kb).

Oocytes were injected with 50 nl of the human VR3 receptor RNA (0.3–5 ng) with or without co-injection of VR1 (2–3 ng). Control oocytes were injected with 50 nl of water. Oocytes were incubated for 1–13 days in ND-96 before analysis for expression of the human VR3. Incubations and collagenase digestion were carried out at room temperature. Injected oocytes were maintained in 48 well cell culture clusters (Costar; Cambridge, Mass.) at 18° C. Whole cell agonist-induced currents were measured 1–14 days after injection with a conventional two-electrode voltage clamp (GeneClamp500, Axon Instruments, Foster City, Calif.) using standard methods previously described and known in the art (Dascal, 1987). The microelectrodes were filled with 3 M KCl, which had resistances of 1 and 2 MΩ. Cells were continuously perfused with ND96 at ~10 ml/min at room temperature unless indicated. Membrane voltage was clamped at −70 mV unless indicated.

Figure 10B:
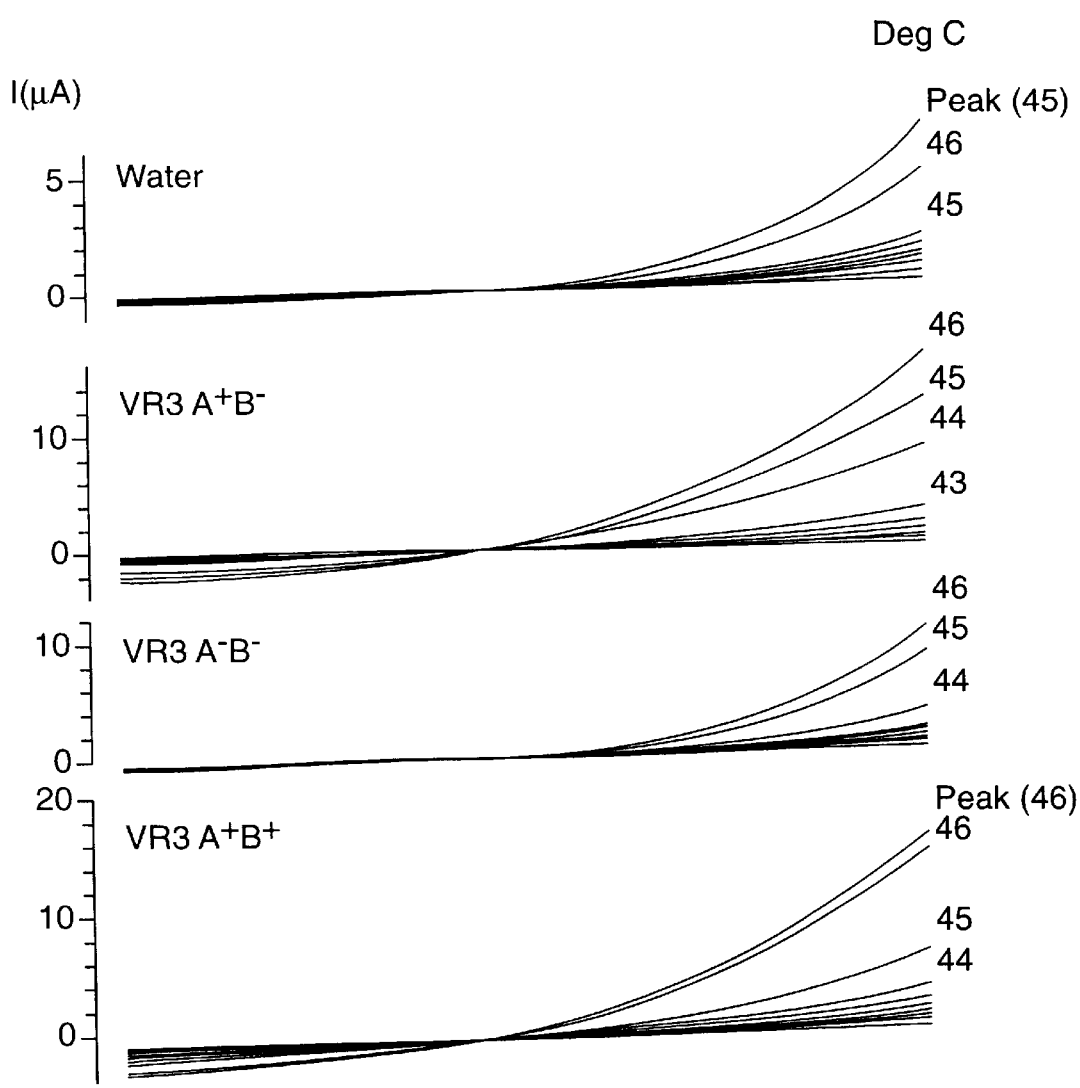
Figure 11A:
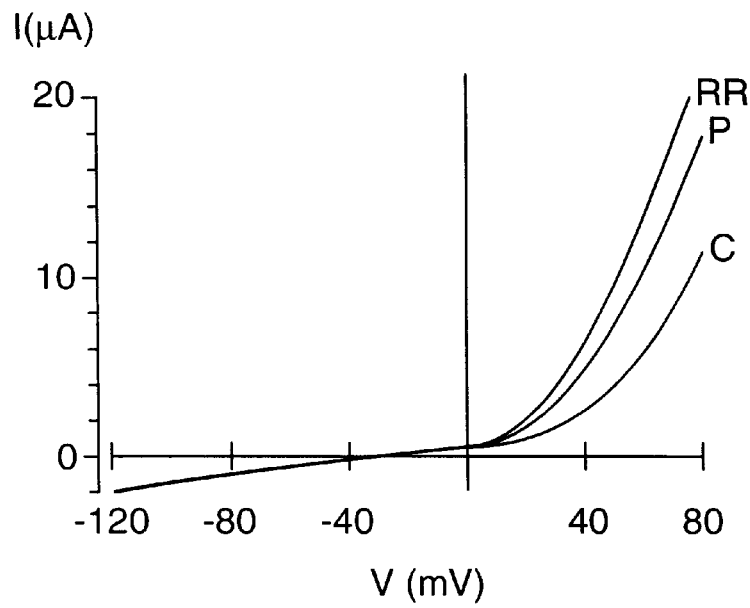
FIGS. 11A and 11B—Function in oocytes: VR3A+B– confers sensitivity to 10 uM ruthenium red to the perfusion activated current ($I_{perfusion}$) observed in VR1-expressing oocytes induced by cell perfusion by extracellular saline solutions. Activation of $I_{perfusion}$ by increased perfusion was blocked by ruthenium red only in VR1- expressing oocytes injected with VR3 A+B– cRNA, and not in oocytes expressing only VR1.
Figure 11B:
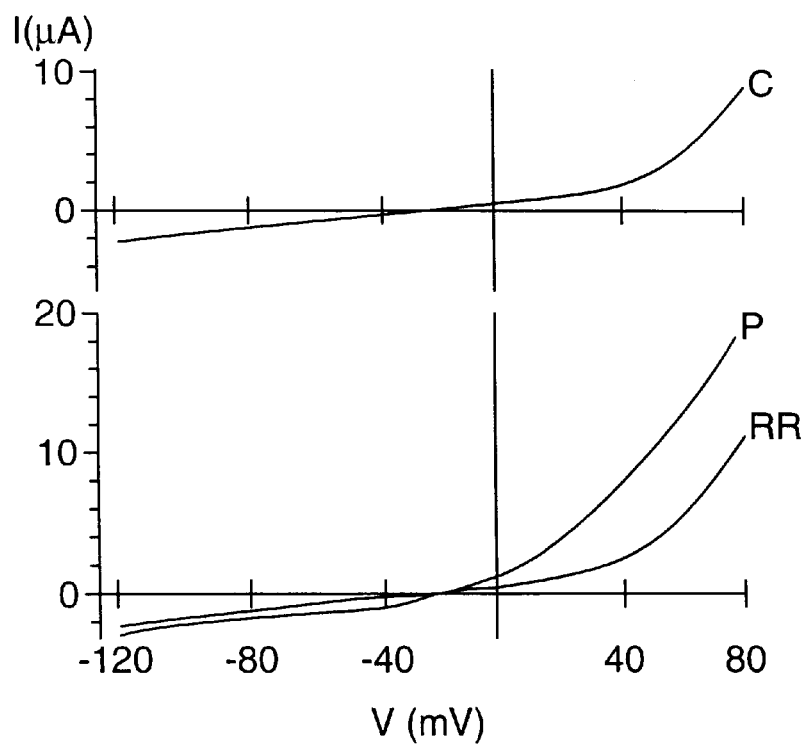
Figure 12A:
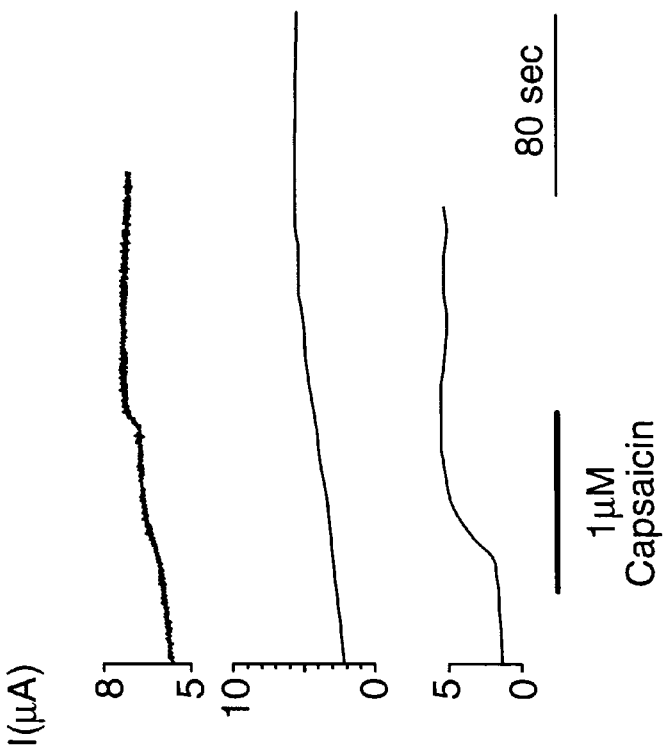
FIGS. 12A and 12B—Function in oocytes.
Figure 12B:
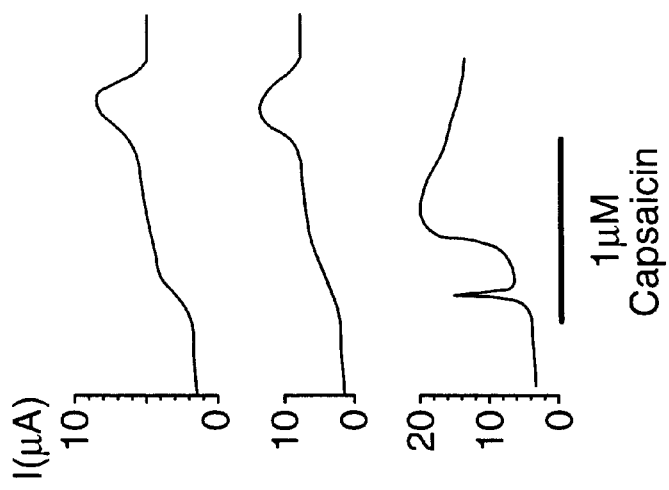

Oocytes were challenged with a variety of ligands, low pH, and depolarizing as well as hyperpolarizing voltage steps but there were no detectable differences in membrane conductance between human VR3-expressing oocytes and control oocytes [see Table 1]. However, human VR3 injected oocytes had properties that were different from controls in 4 respects. First, injection of VR3 A+B− cRNA caused oocytes to die. The viability of oocytes injected with VR3 isoforms having the A insert was significantly reduced compared to sister controls 3–4 days after injection (FIG. 9). Second, all three isoforms of VR3 enhanced the heat-induced response (FIGS. 10A and 10B). Third, A+B− co-injection with human VR1 produced a ruthenium red sensitive perfusion-induced current ($I_{perfusion}$) (FIGS. 11A and 11B). Fourth, human VR3 A+B− cRNA co-injection with human VR1 cRNA altered the responsiveness of the oocytes to 1 uM capsaicin, an agonist at the VR1 receptor (FIGS. 12A and 12B).

TABLE 1

| Stimulus | VR3 A + B − (3.25− 4 ng injected per oocyte unless specified) | VR3 A − B − (1.5 ng injected per oocyte) | VR3 A + B + (5 ng injected per oocyte) |
| --- | --- | --- | --- |
| Capsaicin (1 uM) | NE: n = 3 (n = 30.4 ng) | NE: n = 3 | NE: n = 3 |
| Eugenol (10 uM) | NE: n = 3 (n = 30.4 ng) | NE: n = 3 | NE: n = 3 |
| Olvanil (10 uM) | NE: n = 3 (n = 10.4 ng) | NE: n = 3 | NE: n = 3 |
| Resiniferatoxin (1 uM) | NE: n = 3 (n = 10.4 ng) | NE: n = 3 | NE: n = 3 |
| Piperine (10 uM) | NE: n = 3 (n = 10.4 ng) | NE: n = 3 | NE: n = 3 |
| Gingerol (10 uM) | NE: n = 3 (n = 10.4 ng) | NE: n = 3 | NE: n = 3 |
| Guiaicol (10 uM) | NE: n = 3 (n = 10.4 ng) | NE: n = 3 | NE: n = 3 |
| β-phenylethylamine (100 uM) | NE: n = 2 | NT | NT |
| γ-hydroxybutyrate (100 uM) | NE: n = 2 | NT | NT |
| Anandamide (1.15 uM; RBI) | NE: n = 3 (0.4 ng injected) | NE: n = 1 | NT |
| Arachadonic acid (10 uM) | NT | NE: n = 3 | NT |
| pH 4.5–5.5 | NE: n = 2 (4 ng cRNA); n = 1 (0.4 ng cRNA) | NE: n = 1 | NE: n = 1 |
| Depolarization | No difference from control (n = 4) | No difference from control (n = 6) | No difference from control (n = 3) |
| Hyperpolarization | No difference from control (n = 4) | No difference from control (n = 6) | No difference from control (n = 3) |

NE: no effect; NT: not tested

Viability

Functional expression of human VR3 isoforms in Xenopus oocytes is shown: viability of oocytes maintained in ND-96 containing 2 $Ca^{2+}$ was significantly diminished 4–6 days after injection with VR3 A+B− (3.25 ng) and VR3

A+B+ (5 ng) but not VR3 A−B− (1.5 ng) cRNA. Data for VR3 A+B− and control water-injected ootyes were similar in 5 separate experiments and combined. Dead oocytes were determined visually using a Bauch and Lomb dissecting microscope. Data were analyzed using Chi square analysis. VR3 A+B− injected oocytes were the least viable: only about 9% of oocytes survived to 4–6 days after injection. About 33% of oocytes injected with human VR3 A+B+ survived to 4–6 days after injection. About 67% of sister water-injected control oocytes survived the same time period under essentially identical conditions. VR3 A−B− injected oocytes revealed similar viability to water injected controls. Similar data were obtained from 2 separate batches of cRNA.

Heat Responsiveness

Functional expression of human VR3 isoforms in Xenopus oocytes is shown: activation by heat. a). Shown is the mean peak current elicited by a heat ramp from 25 deg C. to 46 deg C. and maintained at 46 deg C. for at least 15 sec. Voltage ramps were applied from −120 to +80 mV over 400 msec at a sampling rate of 2 sec. The current shown was the increase in current over and above the initial current elicited at +80 mV (the rightmost point on the current voltage curve shown in (b)). Oocytes were injected with 3.25, 1.5 and 5 ng VR3 A+B−, A−B−, and A+B+ cRNA, respectively, and recorded up to 6 days later. Solid bar: water-injected controls (n=8); clear bar: VR3 A+B− isoform (n=1); hatched bar: VR3 A−B− isoform (n=8); stippled bar: VR3 A+B+ isoform (n=5). All isoforms showed a significant increase over water controls (p=0.001, 0.03 and 0.007, respectively). The heat-induced response was about 2-fold larger in the A+B− isoform compared to the other 2 isoforms, but the differences were not significant (p=0.051 and p=0.16, for A+B− compared to A−B− and A+B+, respectively). Data were obtained from 2 sets of injected oocytes. Data shown is the mean and standard error of the mean. (b). Voltage-ramp induced currents were recorded during application of increasing heat to oocytes injected with water (top), VR3 A+B− (second from top), VR3 A−B− ($3^{rd}$ from top), and VR3A+B+ (bottom). Oocytes were constantly perfused with Ca2+ ND-96 and the solution was heated by an inline heater device (TC-324B in conjunction with the SH-27A in line heater; Warner Instrument Corp.). Ramp induced currents (in microAmperes, as indicated on the y-axis) obtained at temperatures from 37 deg C. to 46 deg C. are displayed; only current traces at the higher temperatures are labeled with the corresponding temperature.

Perfusion Induced Currents ($I_{perfusion}$; FIGS. 11A and 14B)

The onset of bath perfusion elicited an increase in membrane conductance in oocytes that had been injected with RNA transcribed from the cloned human VR1 with and without RNA transcribed from VR3A+B− receptor cDNA as shown in FIGS. 11A AND 11B. An oocyte injected with VR1 cRNA (FIG. 11A) was challenged with voltage ramps between −120 and +80 mV over 400 msec. The ramp-induced currents were increased after onset of perfusion of the oocyte at a rate of 10 ml/min. Control ramp induced currents from oocytes in still extracellular saline (C) were recorded prior to the onset of bath perfusion of Ca2+ ND-96. During perfusion, the ramp induced currents increased, indicating an increase in conductance (P). Subsequent perfusion of 10 uM ruthenium red (RR) did not block the perfusion induced current (P) in VR1-expressing oocytes. Thus, the perfusion-induced current observed in oocytes expressing VR1 alone was insensitive to 10 uM ruthenium red (A, "RR"). However, the perfusion-induced current elicited in oocytes expressing VR3A+B− and VR1 were dramatically inhibited by 10 uM ruthenium red (B, "R"). This difference was observed in 6 oocytes. The block was partially reversible (not shown). (FIG. 11B). An oocyte injected with VR1 cRNA together with VR3 A+B− was challenged with voltage ramps between −120 and +80 mV over 400 msec. The ramp-induced currents were increased after onset of perfusion of the oocyte at a rate of 10 ml/min. Perfusion activated currents had similar magnitudes in both sets of oocytes. Vrev for the RR inhibited current was about −13 mV (arrow). The currents induced by both agonists were strongly outwardly rectifying, as reported previously for the rat VR1 (Caterina et al., 1997).

Capsaicin Induced Currents in Oocytes Expressing Human VR1 in the Presence or Absence of Human VR3 A+B− (FIGS. 12A and 12B)

Currents elicited by 1 uM capsaicin (FIGS. 12A and 12B) were measured at a holding voltage of +50 mV since responses were largest at this voltage due to profound outward rectification of the capsaicin-induced currents (Caterina et al., 1997). Shown are 3 examples of oocytes injected with VR1 and water (a control for VR3 injection) (FIG. 12A) and oocytes injected with VR1 cRNA and VR3 A+B− cRNA (FIG. 12B). Capsaicin was bath applied during the time indicated by the solid horizontal bar. The magnitude of the primary response to 1 uM capsaicin was diminished when VR1 cRNA was co-expressed with VR3 A+B− cRNA at equal ratios (2.9 ng each). The most notable difference was the magnitude and decay rate of the secondary response, the second hump that was usually obtained at the beginning of the washout of capsaicin.

EXAMPLE 6

Characterization of Human VR3 in Mammalian Cell Lines

Human HEK293, CHO-K1 and COS-7 cells are transfected with human VR3 isoforms pVR3A+B−R, pVR3A−B−R, or pVR3A+B+R,. Transient transfections 1 μg of pVR3R per $10^6$ cells per 100 mm dish are performed using the Effectene tranfection kit (Quiagen; 301425). Three days after transfection, cells are plated onto 96-well plates (Biocoat, poly-D-lysine coated black/clear plate; Becton Dickinson part #354640). After one day, wells are rinsed with F12/DMEM, then incubated in Fluo-4 (2 μM) with Pluronic F-127 (20%, 40 μl used in 20 mls total volume) for 1 hour at room temperature. Plates are assayed using the FLIPR (Molecular Devices, FL-101).

Cells are challenged with solutions of different osmolarity (40 μl added to 80 μl at a velocity of 50 μl/sec). Some wells are vigorously mixed to simulate increased perfusion of the cells with extracellular solution. Transfections with vector alone are used as controls.

After three days the cells are selected in the presence of neomycin (200 μg/ml) and grown through three 1:10 dilution passages for approximately two weeks. Individual colonies are picked and grown in 6-well dishes. Cells are then plated onto 96-well plates (Biocoat, poly-D-lysine coated black/clear plate; Becton Dickinson part #354640) and grown to confluence for three days. Wells are rinsed with F 12/DMEM, then incubated in Fluo-4 (2 μM) with Pluronic acid (20%, 40 μl used in 20 mls total volume) for 1 hour at room temperature. Plates are assayed using the FLIPR (Molecular Devices, FL-101). Cells are challenged with agonists (at 3-fold concentration in 40 μl added to 80 μl at a velocity of 50 μl/sec).

The whole cell patch clamp technique (Hamill et al., 1981) is used to record ligand-induced currents from HEK293 stably expressing human VR1 receptor maintained for >2 days on 12 mm coverslips. Cells are visualized using a Nikon Diaphot 300 with DIC Nomarski optics. Cells are continuously perfused in a physiological saline (~0.5 ml/min) unless otherwise indicated. The standard physiological saline ("Tyrodes") contains: 130 mM NaCl, 4 mM KCl, 1 mM $CaCl_2$, 1.2 mM $MgCl_2$, and 10 mM hemi-Na-HEPES (pH 7.3, 295–300 mOsm as measured using a Wescor 5500 vapor-pressure (Wescor, Inc., Logan, Utah). Recording electrodes are fabricated from borosilicate capillary tubing (R6; Garner Glass, Claremont, Calif.), the tips are coated with dental periphery wax (Miles Laboratories, South Bend, Ind.), and have resistances of 1–2 MΩ when containing intracellular saline: 100 mM K-gluconate, 25 mM KCl, 0.483 mM $CaCl_2$, 3 mM $MgCl_2$, 10 mM hemi-Na-HEPES and 1 mM $K_4$-BAPTA (100 nM free $Ca^{+2}$); pH 7.4, with dextrose added to achieve 290 mOsm). Liquid junction potentials are −18 mV using standard pipette and bath solutions as determined both empirically and using the computer program JPCalc ((Barry, 1994)). All voltages shown are corrected for liquid junction potential. Current and voltage signals are detected and filtered at 2 kHz with an Axopatch ID patch-clamp amplifier (Axon Instruments, Foster City, Calif.), digitally recorded with a DigiData 1200B laboratory interface (Axon Instruments), and PC compatible computer system and stored on magnetic disk for off-line analysis. Data acquisition and analysis are performed with PClamp software. Slow changes in holding current are detected and filtered at 2 kHz, and recorded with a LPF202A DC amplifier (Warner, Hamden, Conn.) and VR10B digital data recorder (Instrutech, Great Neck, N.Y.) onto video tape. The signal is later analyzed at 10 Hz using Axotape software.

The total membrane capacitance ($C_m$) is determined as the difference between the maximum current after a 30 mV hyperpolarizing voltage ramp from −68 mV generated at a rate of 10 mV/ms and the steady state current at the final potential (−98 mV) (Dubin et al., 1999).

Apparent reversal potentials ($V_{rev}$) of ligand-induced conductance changes are determined using a voltage-ramp protocol (Dubin et al., 1999). Voltage ramps are applied every 1 second and the resulting whole cell ramp-induced currents were recorded. Usually the voltage was ramped from negative to positive to negative values. The current required to clamp the cells at −68 mV is continuously monitored. Ligand-induced conductances are determined from whole-cell currents elicited by a voltage-ramp protocol in the presence and absence of ligand. Voltage ramp-induced currents measured before (control) and in the presence of ligand are compared to reveal the effect of the ligand on the channel to modulate the channel current output. The voltage at which there is no net ligand-induced current is determined ($V_{rev}$).

EXAMPLE 7

Primary Structure of the Human VR3 Receptor Protein

The present invention describes 3 isoforms of hVR3: A+B−, A−B−, and A+B+. The nucleotide sequences of human VR3 receptor cDNAs revealed single large open reading frame of about 2616, 2436 and 2229 base pairs encoding 871, 811, and 742 amino acids for human VR3 A+B−, A−B− and A+B+, respectively. The cDNA for VR3 A+B− has 5' and 3'-untranslated extensions of about 337 and about 547 nucleotides. The cDNA for VR3 A+B+has 5' and 3'-untranslated extensions of about 836 and about 994 nucleotides. The first in-frame methionine was designated as the initiation codon for an open reading frame that predicts human VR3 receptor proteins with an estimated molecular mass ($M_r$) of about 98,242 Da, 91,294 Da and 83,310 Da for the isoforms A+B−, A−B− and A+B+, respectively. The A+B− isoform encodes a protein of 871 amino acids. The VR3 A−B− contains a deletion of 60 amino acids from amino acid 382 to 441 of VR3A+B−. VR3 A+B+ is identical to A+B− until amino acid 736 after which there are 6 divergent amino acids and a stop codon. The VR3 A+B+ isoform extends 20 amino acids after the putative TM6.

The predicted human VR3 receptor proteins were aligned with nucleotide and protein databases and found to be related to the vanilloid receptor family (VR1 and VR2). There are several conserved motifs found in this family of receptor including a large putative N-terminal hydrophilic segment (about 467 amino acids), three putative ankyrin repeat domains in the N-terminus region, 6 predicted transmembrane regions and a pore region. VR3 A+B− is 43% identical to human VR1, 39% identical to both human VRL-1 (AF129112) and human VRL (AF103906). Thus the VR3 receptor described herein is clearly a novel gene of the vanilloid receptor family.

VR3A+B− and VR3A−B− forms are very similar to the rat stretch-inhibitable channel SIC [genbank accession AB015231] from amino acid 694 to the end. SIC, ecoded by 529 amino acids, is thought to form an ion channel inhibited by stretch. It lacks the large N-terminal cytoplasmic domain of the VR family but contains a sequence homologous to the A exon prior to the putative TM1.

The complete genomic sequence of the VR3 coding regions described herein appears to be found in a 380512 base pair sequence submission to genbank (homo sapiens clone RPCI1-7G5 (AC007834), direct submission by Worley, K. C.). This genbank entry list many fragments of DNA sequence and a proposed contiguous sequence, but lacks any analysis of the nucleic acid sequence and fails to characterize the features of the VR3 nucleic acid sequences, or describe the presence of the VR3 gene.

1 Comparison of the sequences the present invention and the genomic sequence reveal that VR3 gene is composed of at least 15 exons. "A" is a 60 amino acid insert in the putative N-terminal cytoplasmic domain that found in cDNAs obtained from both pituitary and prostate cDNA libraries. There are intron/exon border sequences at the A and B inserts.

The A+B− and A+B+ isoforms contain a domain in the N-terminal putative cytoplasmic region with homology to ankyrin repeat domain consensus sequences. Thus, the VR3 A+ isoforms appear to have a similar architecture as that predicted for VR1. The first domain was significantly similar to the consensus sequence (E=2.6 e-5). The next 2 domains are not significant taken by themselves (e=37 and E=2.7) however taken as a whole, this region is likely to contain 3 ankyrin binding domains. The A− isoform is missing 20 amino acids of the putative $3^{rd}$ ankryn repeat domain and the juxtaposed sequence does not conform to an ankyrin repeat domain.

The VR3 A+B− isoform has two potential myristoylation sites; [GPGGE] in N terminal and between TM4 and TM5. Putative phosphorylation sites include: 7 potential PKC phosphorylation sites: T112, S134, T175, T190, T380, S403, S688 [however, S688 is in a putative extracellular region]; 1 potential PKA and PKG phosphorylation site: T181; 12 potential casein kinase II phosphorylation sites: T89, S162, T181, T395, S416, S422, S432, T426, S432, S441, T740, S836; 3 potential mammary gland casein kinase phosphorylation sites (SxE): S4, S726, S758; 1 potential tyrosine kinase phosphorylation site: Y411 [present in the "A" insert]; and 1 potential N-linked glycosylation site: N651, [N201, N207 are in the putative intracellular N-terminal domain and are unlikely to be glycosylated]. There are no putative CaM binding domains in any isoform described in the present invention.

In the A− isoform lacking the "A" insert 2 PKC phosphorylation sites, 6 casein kinase II phosphorylation sites, and the only putative tyrosine kinase phosphorylation site is lacking.

The A+B+ isoform encodes a putative protein that lacks 2 casein kinase II phosphorylation sites in the C-terminal putative intracellular region.

EXAMPLE 8

Expression of Human VR3 in Tissues

Expression using a DNA array (Luo et al., 1999). DNA array distribution analysis indicates that human VR3 mRNAs were expressed in a variety of tissues, and there was some overlap of expression with VR1 at a whole tissue level [FIG. 13]. The cRNA from the tissue type indicated in the left column contained sequences encoding the human VR3 (middle column). Expression of human VR1 is shown in the right column and in most cases overlapped with VR3 expression. NOTE: NS was non-significant expression of human VR1. The sequence of human VR3 DNA immobilized on the DNA array was (SEQ.ID.NO.:17)

```
CCACCATCCTGGACATTGAGCGCTCCT-
  TCCCCGTATTCCTGAGGAAGGCCT TCCGCTCTGGG-
  GAGATGGTCACCGTGGGCAAGAGCTCG-
  GACGGCACTCCT
  GACCGCAGTGGTGCTTCAGGGTGGAT-
  GAGGTGAACTGGTCTCACTGGAAC CAGAACT-
  TGGGCATCATCAACGAGGACCCGGGCAA-
  GAATGAGACCTACC AGTATTATGG
  CTTCTCGCATACCGTGGGCCGCC.
```

This DNA sequence is not present in A+B+, only A+B− and A−B− isoforms. Note that the cDNA species was cloned from prostate gland (*; FIG. 13).

Northern blot analysis revealed expression of VR3 in whole brain, placenta, lung, kidney, pancreas and prostate.

EXAMPLE 9

Cloning Human VR3 Receptor cDNA into E. coli Expression Vectors

Recombinant human VR3 receptor is produced in E. coli following the transfer of the human VR3 receptor expression cassette into E. coli expression vectors, including but not limited to, the pET series (Novagen). The pET vectors place human VR3 receptor expression under control of the tightly regulated bacteriophage T7 promoter. Following transfer of this construct into an E. coli host that contain a chromosomal copy of the T7 RNA polymerase gene driven by the inducible lac promoter, expression of human VR3 receptor is induced when an appropriate lac substrate (IPTG) is added to the culture. The levels of expressed human VR3 receptor are determined by the assays described herein.

The cDNA encoding the entire open reading frame for human VR3 receptor is inserted into the NdeI site of pET [16] 11a. Constructs in the positive orientation are identified by sequence analysis and used to transform the expression host strain BL21. Transformants are then used to inoculate cultures for the production of human VR3 receptor protein. Cultures may be grown in M9 or ZB media, whose formulation is known to those skilled in the art. After growth to an $OD_{600}=1.5$, expression of human VR3 receptor is induced with 1 mM IPTG for 3 hours at 37° C.

EXAMPLE 10

Cloning Human VR3 Receptor cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL#1711). Recombinant baculoviruses expressing human VR3 receptor cDNA is produced by the following standard methods (In Vitrogen Maxbac Manual): the human VR3 receptor cDNA constructs are ligated into the polyhedrin gene in a variety of baculovirus transfer vectors, including the pAC360 and the BlueBac vector (In Vitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, human VR3 receptor expression is measured by the assays described herein.

The cDNA encoding the entire open reading frame for human VR3 receptor is inserted into the BamItI site of pBlueBacII. Constructs in the positive orientation are identified by sequence analysis and used to transfect Sf9 cells in the presence of linear AcNPV mild type DNA.

Authentic, active human VR3 receptor is found in the cytoplasm of infected cells. Active human VR3 receptor is extracted from infected cells by hypotonic or detergent lysis.

EXAMPLE 11

Cloning Human VR3 Receptor cDNA into a Yeast Expression Vector

Recombinant human VR3 receptor is produced in the yeast S. cerevisiae following insertion of the optimal human VR3 receptor cDNA cistron into expression vectors designed to direct the intracellular or extracellular expression of heterologous proteins. In the case of intracellular expression, vectors such as EmBLyex4 or the like are ligated to the human VR3 receptor cistron [Rinas, U. et al., Biotechnology 8: 543–545 (1990); Horowitz B. et al., J. Biol. Chem. 265: 4189–4192 (1989)]. For extracellular expression, the human VR3 receptor cistron is ligated into yeast expression vectors which fuse a secretion signal (a yeast or mammalian peptide) to the $NH_2$ terminus of the human VR3 receptor protein [Jacobson, M. A., Gene 85: 511–516 (1989); Riett L. and Bellon N. Biochem. 28: 2941–2949 (1989)].

These vectors include, but are not limited to pAVE 1>6, which fuses the human serum albumin signal to the expressed cDNA [Steep O. Biotechnology 8: 42–46 (1990)], and the vector pL8PL which fuses the human lysozyme signal to the expressed cDNA [Yamamoto, Y., Biochem. 28: 2728–2732)]. In addition, human VR3 receptor is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed human VR3 receptor are determined by the assays described herein.

EXAMPLE 12

Purification of Recombinant Human VR3 Receptor

Recombinantly produced human VR3 receptor may be purified by antibody affinity chromatography.

Human VR3 receptor antibody affinity columns are made by adding the anti-human VR3 receptor antibodies to Affigel-10 (Bio-Rad), a gel support that is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatant or cell extract containing solubilized human VR3 receptor is slowly passed through the column. The column is then washed with phosphate-buffered saline together with detergents until the optical density (A280) falls to background, then the protein is eluted with 0.23 M glycine-HCl (pH 2.6) together with detergents. The purified human VR3 receptor protein is then dialyzed against phosphate buffered saline.

REFERENCES

Bevan, S., Hothi, S., Hughes, G., James, I. F., Rang, H. P., Shah, K., Walpole, C. S. J., and Yeats, J. C. (1992). Capsazepine: a competitive antagonist of the sensory neuron excitant capsaicin. Br. J. Pharmacol. 107, 544–52.

Bevan, S., and Szolcsanyi, J. (1990). Sensory neuron-specific actions of capsaicin: mechanisms and applications. Trends Pharmacol. Sci. 11, 330–3.

Blackstone, C., and Sheng, M. (1999). Protein targeting and calcium signaling microdomains in neuronal cells. Cell Calcium 26, 181–192.

Caterina, M. J., Rosen, T. A., Tominaga, M., Brake, A. J., and Julius, D. (1999). A capsaicin-receptor homolog with a high threshold for noxious heat. Nature (London) 398, 436–441.

Caterina, M. J., Schumacher, M. A., Tominaga, M., Rosen, T. A., Levine, J. D., and Julius, D. (1997). The capsaicin receptor: a heat-activated ion channel in the pain pathway. Nature (London) 389, 816–824.

Fraser, S. P., Moon, C., and Djamgoz, M. B. A. (1993). Electrophysiology of Xenopus oocytes: An expression system in molecular neurobiology., D. Wallis, ed. (Oxford, UK: IRL).

Gupta, P. D., and Pushkala, K. (1999). Importance of the role of calcium in programmed cell death: a review. Cytobios 99, 83–95.

Lu, M., and Wong, F. (1987). A DNA deletion associated with multiple impaired transcripts in the visual mutant trp. Invest. Ophthalmol. Visual Sci. 28, 2092–5.

Luo, L., Salunga, R. C., Guo, H., Bitner, A., Joy, K. C., Galindo, J. E., Xiao, H., Rogers, K. E., Wan, J. S., Jackson, M. R., and Erlander, M. G. (1999). Gene expression profiles of laser-captured adjacent neuronal subtypes. Nat. Med. (N.Y.) 5,117–121.

Minke, B., and Selinger, Z. (1996). The roles of trp and calcium in regulating photoreceptor function in Drosophila. In Curr. Opin. Neurobiol., pp. 459–466.

Oh, U., Hwang, S. W., and Kim, D. (1996). Capsaicin activates a nonselective cation channel in cultured neonatal rat dorsal root ganglion neurons. J. Neurosci. 16, 1659–67.

Suzuki, M., Sato, J., Kutsuwada, K., Ooki, G., and Imai, M. (1999). Cloning of a stretch-inhibitable nonselective cation channel. J. Biol. Chem. 274, 6330–6335.

Szallasi, A. (1995). Autoradiographic visualization and pharmacological characterization of vanilloid (capsaicin) receptors in several species, including man. Acta Physiol. Scand., Suppl. 155, 1–68.

Szolcsanyi, J. (1993). Actions of capsaicin on sensory receptors. In Capsaicin Study Pain, J. N. Wood, ed.: Academic, London, UK), pp. 1–26.

Szolcsanyi, J. (1996). Capsaicin-sensitive sensory nerve terminals with local and systemic efferent functions: facts and scopes of an unorthodox neuroregulatory mechanism. Prog. Brain Res. 113, 343–359.

Szolcsanyi, J., Szallasi, A., Szallasi, Z., Joo, F., and Blumberg, P. M. (1 991). Resiniferatoxin. An ultrapotent neurotoxin of capsaicin-sensitive primary afferent neurons. Ann. N.Y. Acad. Sci. 632, 473–5.

Tominaga, M., Caterina, M. J., Malmberg, A. B., Rosen, T. A., Gilbert, H., Skinner, K., Raumann, B., Basbaum, A. I., and Julius, D. (1998). The cloned capsaicin receptor integrates multiple pain-producing stimuli. Neuron 21, 531–543.

van Haasteren, G., Li, S., Muda, M., Susini, S., and Schlegel, W. (1999). Calcium signalling and gene expression. In J. Recept. Signal Transduction Res., pp. 481–492.

Wall, P. D., and Melzack, R. (1994). Textbook of Pain (New York: Churchill Livingstone).

Wood, J. N., Winter, J., James, I. F., Rang, H. P., Yeats, J., and Bevan, S. (1988). Capsaicin-induced ion fluxes in dorsal root ganglion cells in culture. J. Neurosci. 8, 3208–20.

What is claimed is:

1. An isolated and purified nucleic acid molecule which encodes a human Vanilloid Receptor 3 (VR3) protein, wherein said protein comprises the amino acid sequence set forth in SEQ ID NO: 7.

2. The isolated and purified nucleic acid molecule of claim 1, having a nucleotide sequence selected from a group consisting of SEQ ID NO: 5 and SEQ ID NO: 6.

3. The isolated and purified nucleic acid molecule of claim 1, wherein said molecule is selected from a group consisting of DNA, RNA, and cDNA.

4. An expression vector comprising a nucleic acid sequence encoding human Vanilloid Receptor 3 (VR3) protein, wherein said protein comprises the amino acid sequence set forth in SEQ ID NO: 7.

5. The expression vector of claim 4, wherein the nucleic acid sequence encoding human VR3 protein is selected from a group consisting of SEQ ID NO: 5 and SEQ ID NO: 6.

6. The expression vector of claim 4, wherein the expression vector contains DNA encoding human VR3 protein.

7. A process for expression of human Vanilloid Receptor 3 (VR3) protein in a recombinant host cell comprising:

a) transferring the expression vector of claim 4 into suitable host cells; and b) culturing the host cells of step (a) under conditions which allow expression of the human VR3 protein from the expression vector.

8. The recombinant host cell of claim 7, wherein said expression vector comprises a nucleotide sequence selected from a group consisting of SEQ ID NO: 5 and SEQ ID NO: 6.

9. A process for expression of human Vanilloid Receptor 3 (VR3) protein in a recombinant host cell comprising:

transferring the expression vector of claim 4 into suitable host cells; and culturing the host cells of step (a) under conditions which allow expression of the human VR3 protein from the expression vector.

* * * * *

UNITED STATES PATENT AND TRADEMARK OFFICE
CERTIFICATE OF CORRECTION

PATENT NO. : 6,455,278 B1
DATED : September 24, 2002
INVENTOR(S) : Dubin et al.

It is certified that error appears in the above-identified patent and that said Letters Patent is hereby corrected as shown below:

Column 33,
Line 1, delete the entire claim and replace with
 7. A recombinant host cell comprising the expression vector of claim 4.

Column 34,
Line 3, insert -- a) -- at the beginning of line 3 of the claim; and
Line 5, insert -- b) -- at the beginning of line 5 of the claim.

Signed and Sealed this

Twenty-second Day of June, 2004

JON W. DUDAS
*Acting Director of the United States Patent and Trademark Office*